(12) United States Patent
Klappert et al.

(10) Patent No.: US 11,083,413 B2
(45) Date of Patent: *Aug. 10, 2021

(54) METHODS AND SYSTEMS FOR SELECTING MEDIA GUIDANCE APPLICATIONS BASED ON A POSITION OF A BRAIN MONITORING USER DEVICE

(71) Applicant: Rovi Guides, Inc., San Jose, CA (US)

(72) Inventors: Walter R. Klappert, North Hollywood, CA (US); Kanako Tomita, Tokyo (JP); David John Wheatley, Tower Lakes, IL (US)

(73) Assignee: Rovi Guides, Inc., San Jose, CA (US)

( * ) Notice: Subject to any disclaimer, the term of this patent is extended or adjusted under 35 U.S.C. 154(b) by 230 days.

This patent is subject to a terminal disclaimer.

(21) Appl. No.: 16/447,906

(22) Filed: Jun. 20, 2019

(65) Prior Publication Data

US 2019/0298254 A1 Oct. 3, 2019

Related U.S. Application Data

(63) Continuation of application No. 14/230,748, filed on Mar. 31, 2014, now Pat. No. 10,368,802.

(51) Int. Cl.
*A61B 5/04* (2006.01)
*A61B 5/00* (2006.01)
(Continued)

(52) U.S. Cl.
CPC ............ *A61B 5/486* (2013.01); *A61B 5/165* (2013.01); *A61B 5/316* (2021.01); *A61B 5/6803* (2013.01);
(Continued)

(58) Field of Classification Search
CPC ......... A61B 5/486; A61B 5/316; A61B 5/684; A61B 5/7246; A61B 5/7267; A61B 5/165; A61B 5/6803; A61B 5/7278; A61B 5/7221; A61B 5/7435; A61B 5/0006; A61B 5/0022; A61B 5/01; A61B 5/14553; A61B 5/4064; A61B 2560/0209; A61B 2560/0276; A61B 2560/0487; A61B 5/369; G06F 3/013; G06F 3/015; G06F 2203/011; H04N 21/25891; H04N 21/42201; H04N 21/44222; H04N 21/4532; H04N 21/6582; H04N 21/472; H04N 21/4312; H04N 21/4668; H04N 21/4755; H04N 21/485; G16H 50/70
See application file for complete search history.

(56) References Cited

PUBLICATIONS

"P3-P4 and midline," 2010, Web, Retrieved from: https://www.emotiv.com/forums/topic/P3_P4_and_midline/ (Year: 2010).*

(Continued)

*Primary Examiner* — Navin Natnithithadha
*Assistant Examiner* — Andrey Shostak
(74) *Attorney, Agent, or Firm* — Haley Guiliano LLP

(57) ABSTRACT

Methods and systems are disclosed herein for a system configured to determine a position of a brain monitoring user device, and a brain state of a user. Based on the determined position and the determined brain state, the system provides access to a set of media guidance application operations corresponding to the determined brain state and to brain regions corresponding to the determined position of the brain monitoring user device.

18 Claims, 14 Drawing Sheets

(51) Int. Cl.

| | |
|---|---|
| A61B 5/16 | (2006.01) |
| G06F 3/01 | (2006.01) |
| H04N 21/258 | (2011.01) |
| H04N 21/422 | (2011.01) |
| H04N 21/442 | (2011.01) |
| H04N 21/45 | (2011.01) |
| H04N 21/658 | (2011.01) |
| A61B 5/316 | (2021.01) |
| A61B 5/01 | (2006.01) |
| A61B 5/1455 | (2006.01) |
| H04N 21/431 | (2011.01) |
| H04N 21/466 | (2011.01) |
| H04N 21/475 | (2011.01) |
| H04N 21/485 | (2011.01) |
| H04N 21/472 | (2011.01) |

(52) U.S. Cl.
CPC ............ *A61B 5/684* (2013.01); *A61B 5/7246* (2013.01); *A61B 5/7267* (2013.01); *A61B 5/7278* (2013.01); *G06F 3/013* (2013.01); *G06F 3/015* (2013.01); *H04N 21/25891* (2013.01); *H04N 21/42201* (2013.01); *H04N 21/44222* (2013.01); *H04N 21/4532* (2013.01); *H04N 21/6582* (2013.01); *A61B 5/0006* (2013.01); *A61B 5/0022* (2013.01); *A61B 5/01* (2013.01); *A61B 5/14553* (2013.01); *A61B 5/4064* (2013.01); *A61B 5/7221* (2013.01); *A61B 5/7435* (2013.01); *A61B 2560/0209* (2013.01); *A61B 2560/0276* (2013.01); *A61B 2560/0487* (2013.01); *G06F 2203/011* (2013.01); *H04N 21/4312* (2013.01); *H04N 21/4668* (2013.01); *H04N 21/472* (2013.01); *H04N 21/4755* (2013.01); *H04N 21/485* (2013.01)

(56) References Cited

PUBLICATIONS

"Emotiv Unveils World's First Brain-Controlled Video Gaming Headset," 2008, Web, Retrieved from: http://www.businesswire.com/news/home/20080220005408/en/Emotiv-Unveils-Worlds-Brain-Controlled-Video-Gaming-Headset (Year: 2008).*

Stevens et al, "Entertainment Computing—ICEC 2008," 7th International Conference Proceedings, Pittsburgh, PA, USA, p. 227) (Year: 2008).*

Zhukov, Leonid, David Weinstein, and Chris Johnson. "Independent component analysis for EEG source localization." IEEE Engineering in Medicine and Biology Magazine 19.3 (2000): 87-96 (Year: 2000).*

\* cited by examiner

600

630

660

METHODS AND SYSTEMS FOR SELECTING MEDIA GUIDANCE APPLICATIONS BASED ON A POSITION OF A BRAIN MONITORING USER DEVICE

CROSS-REFERENCE TO RELATED APPLICATIONS

This application is a continuation of U.S. patent application Ser. No. 14/230,748, filed Mar. 31, 2014. The entire contents of which are hereby incorporated by reference herein in their entirety.

BACKGROUND

In conventional systems, consumers of media have a plethora of content options available. For example, the rise in content available via cable, satellite, on-demand, and/or Internet systems provides users with ever increasing amounts of content options. Moreover, as the types of devices on which users may access this media changes, conventional methods (e.g., handheld remote controls, touchscreen interfaces, etc.) may no longer meet all of the user's needs. For example, a small display screen (e.g., common with many mobile devices), with spatial limits for the amount of content that may be displayed, may reduce the efficiency with which a user may search and access media.

Brain monitoring devices have been developed to monitor the brain state of a user and perform operations in response to a detected brain state. Brain monitoring devices used for research include a large number of detectors. The detectors are positioned at various locations on the cranium of a user in order to obtain enough spatially diverse brain signals. Commercial devices use a smaller number of detectors in order to reduce cost and to provide a more aesthetic interface for a user. However, by using a smaller number of detectors, these commercial devices are limited in the number of spatially diverse brain signals and the number of different brain regions that they can monitor. Accordingly, the number of brain activity detectors that are used by commercial devices to monitor brain signals continues to decrease, thereby reducing the number of operations that can be controlled by the decreased number of monitored brain signals. In contrast, the number of operations provided by media devices, and accordingly the number of monitored brain signals needed to control these operations, continues to increase.

SUMMARY

Accordingly, methods and systems are disclosed herein for a media guidance application configured to monitor brain activity in order to navigate, recommend, provide access to, and perform operations related to media content. By monitoring brain activity, in contrast to relying on one or more conventional user input types (e.g., handheld remote controls, physical buttons, touchscreen interfaces, etc.), a media guidance application as disclosed herein may more intuitively and more efficiently provide various operations (e.g., changing channels, controlling volume, etc.).

Furthermore, in order to overcome the limitations of the prior art, the media guidance application may provide different operations to a user based on the position of the brain monitoring user device. For example, because the number of brain activity detectors, and thus the number of spatially diverse brain signals monitored by the user device, may be limited on more aesthetically pleasing devices, a user may move the position of the brain monitoring user device in order to perform operations triggered by different brain signals. This facilitates using a lower number of brain activity detectors, and in turn leads to smaller and more aesthetically pleasing devices, without sacrificing functionality.

In some aspects, a system is configured to provide different sets of media guidance application operations based on a position of a user device (e.g., a position on the cranium of a user). The system stores a database of the sets of media guidance application operations that are available to the user device based on various positions of user devices. For example, the database may store records that correlate a first set of channel changing operations to a first position of the user device, and a second set of volume changing operations to a second position of the user device. The system determines whether a first brain signal from a first brain region is detectable. For example, the system may determine whether a first brain signal measured by a first brain activity detector, disposed on the user device, corresponds to a detectable threshold.

The system then determines a position of the user device on the user that corresponds to the detection of the first brain signal. For example, the system may determine detection of a particular brain signal at a particular brain activity detector indicates that the user device is in a particular position. The system cross-references the determined position of the user device with the database to determine a set of interactive media guidance application operations that are accessible based on the determined position. For example, the system may cross-reference the determined position of the user device with the database and determine that the first position corresponds to channel changing operations and accordingly provide channel changing operations to the user.

In some embodiments, the system is further configured to determine whether a second brain signal from a second brain region is detectable. For example, the system may determine whether a second brain signal measured by a second brain activity detector, disposed on the user device, corresponds to a detectable threshold. The system then updates the position of the user device on the user to correspond with the detection of the first brain signal and the second brain signal. For example, the user device may be a headband that includes the first brain activity detector initially at a first end and the second brain activity detector initially at a second end opposite the first end. The system may later determine that the first brain activity detector is located at the back of the user's cranium, and that the second brain activity detector is located at the front of the user's cranium, and accordingly, update the position of the user device to be backwards on the user's cranium.

In some embodiments, the system is further configured to determine the position of the brain monitoring user device by cross-referencing the detection of the first brain signal with a database listing positions of the user device that correspond to different brain signals being detectable to determine the position of the user device on the user. For example, as discussed above, the brain monitoring user device may include a first brain activity detector and a second brain activity detector, each of which may detect a first brain signal and a second brain signal, respectively. A brain activity detector may detect a different brain signal at each position on a user's cranium. The database may include a list of records correlating brain signals with corresponding positions on a user's cranium. The system may determine the position of the first and second brain activity detectors by cross referencing first and second brain signals detected by the first and second brain activity detectors, respectively, with the records in the database to determine positions of the first and second brain activity detectors on the cranium of a user. Based on the positions of the first and second brain activity detectors on the cranium of a user, and the known locations of the first and second brain activity detectors on the brain monitoring user device, the system may determine the position of the brain monitoring user device on the cranium of a user.

In some embodiments, the brain signal includes an electroencephalogram (EEG) signal and an electromyogram (EMG) signal. For example, the media guidance application (or a user device or control circuitry upon which the media guidance application is implemented) may incorporate and/or have access to an electroencephalogram unit ("EEG") indicating a first frequency range of voltage fluctuations in the brain activity of a user and/or an electromyogram unit ("EMG") indicating first electrical activity of muscles near a brain of the user at rest and during contraction. Furthermore, the EEG and/or the EMG may be incorporated into a battery-powered mobile headset (e.g., styled as traditional headphones, hats/helmets, glasses, etc. or shaped as wearable accessories such as jewelry, earrings, headlaces, hair-clips, etc.) upon which the media guidance application is implemented and/or in communication with. The media guidance may initiate monitoring in response to a user input entered on the user device (e.g., turning the user device on), in response to detecting a change (or lack thereof) in brain activity, and/or based on a predetermined schedule (e.g., when a user typically wakes up from sleeping).

In some embodiments, the first brain signal includes a measurement of at least one of an alpha band constituent signal, a beta band constituent signal, a delta band constituent signal, a gamma band constituent signal, and a theta band constituent signal. For example, the first brain signal may be divided into the constituent signals by relative percentages (e.g., of total intensity, energy, power, $V^2/Hz$, etc.), where the sum of the relative percentages is 100%. For example, the first brain signal may include a 10% alpha band constituent signal, 10% beta band constituent signal, 10% gamma band constituent signal, and 70% theta band constituent signal.

In some embodiments, the system includes a user device configured as a substantially circular fixture. The substantially circular fixture includes at least a first brain activity detector, which is used to determine whether a first brain signal from a first brain region is detectable. For example, the user device may be a headband, and may include a first brain activity detector disposed at an inside surface at the front of the headband.

In some embodiments, the user device is shaped as jewelry. For example, the user device may be shaped as an earring, pendant, or headlace. The jewelry may include a number of brain activity detectors depending on the size of the jewelry. For example, the headlace may include four brain activity detectors, disposed at equal distances around the headlace, and the earring may include only one brain activity detector.

In some embodiments, the position of the user device corresponds to a reference location on the cranium of the user. For example, the user device may be shaped as an adhesive pendant and include a first brain activity detector. The position of the pendant may correspond to a standardized set of known locations on the user's cranium. Each of the known locations may correspond to a unique measured brain signal. The position of the pendant may also correspond to a location or brain region on the cranium that corresponds to one or more of the frontal lobe, occipital lobe, parietal lobe, or temporal lobe.

In some embodiments, the system is configured to determine a brain state of the user based on the first brain signal. For example, as described herein a media guidance application configured to monitor brain activity may perform various operations, including, but not limited to, recommending media assets that correspond to a brain state (e.g., a mood) of a user, providing on-screen options that display or provide access to operations without the need for a user to interact with the options via conventional means, monitoring the attentiveness of a user, compensating for unusual brain activity in distinct areas of the brain, adjusting power levels in a user device based on the brain activity of a user, and/or any combinations thereof. Furthermore, the method and systems described herein may be applied to a vast array of social and scientific fields such as advertising, personal/commercial entertainment, and/or medical therapy.

In some embodiments, the system includes multiple brain activity detectors disposed on a substantially circular fixture and is configured to determine a position of each of the brain activity detectors on a user's cranium. The system may estimate the position on the cranium of each of the brain activity detectors based on each of a corresponding brain signals detected at each respective brain activity detector. The system may refine the estimate of the positions based on the relative and absolute locations of each brain activity detector on the fixture. For example, as discussed above, the user device may be a substantially circular fixture, such as a headband, which includes a first brain activity detector disposed on an inside surface of a front of the headband and a second brain activity detector disposed on the inside surface of a back of headband. The system may determine that the first brain activity detector is positioned at the back of the head, and that the second brain activity detector is positioned at the front of the head. Based on the locations of the brain activity detectors on the headband, and the positions of the brain activity detectors on the head of the user, the system may determine that the brain monitoring user device is positioned with the front of the device at the back of the user's head.

In some embodiments, a media guidance application may monitor the brain activity of a user and determine a brain state of the user based on the brain activity. The brain state (e.g., the current frequency range of voltage fluctuations in the brain and/or electrical activity of muscles of the brain at rest and during contraction) may correspond to a mood of the user. The media guidance application may determine the brain state of the user in part based on the position of each of the brain activity detectors. For example, if the brain activity detectors are located on the temporal lobe (associated with hearing) versus the frontal lobe (associated with emotions), the system may more readily discern whether the user is involved with activities related to auditory stimulation and/or more readily discern whether or not operations based on temporal lobe brain signals are detected. For example, based on the position of the brain activity detectors at the temporal lobe, the system may provide a set of media guidance application operations that are controlled by brain signals associated with the temporal lobe.

It should be noted, the systems, methods, apparatuses, aspects and/or embodiments described above may be applied to, or used in accordance with, other systems, methods, apparatuses, aspects and/or embodiments.

BRIEF DESCRIPTION OF THE DRAWINGS

The above and other objects and advantages of the disclosure will be apparent upon consideration of the following detailed description, taken in conjunction with the accompanying drawings, in which like reference characters refer to like parts throughout, and in which.

DETAILED DESCRIPTION OF DRAWINGS

Figure 1A:
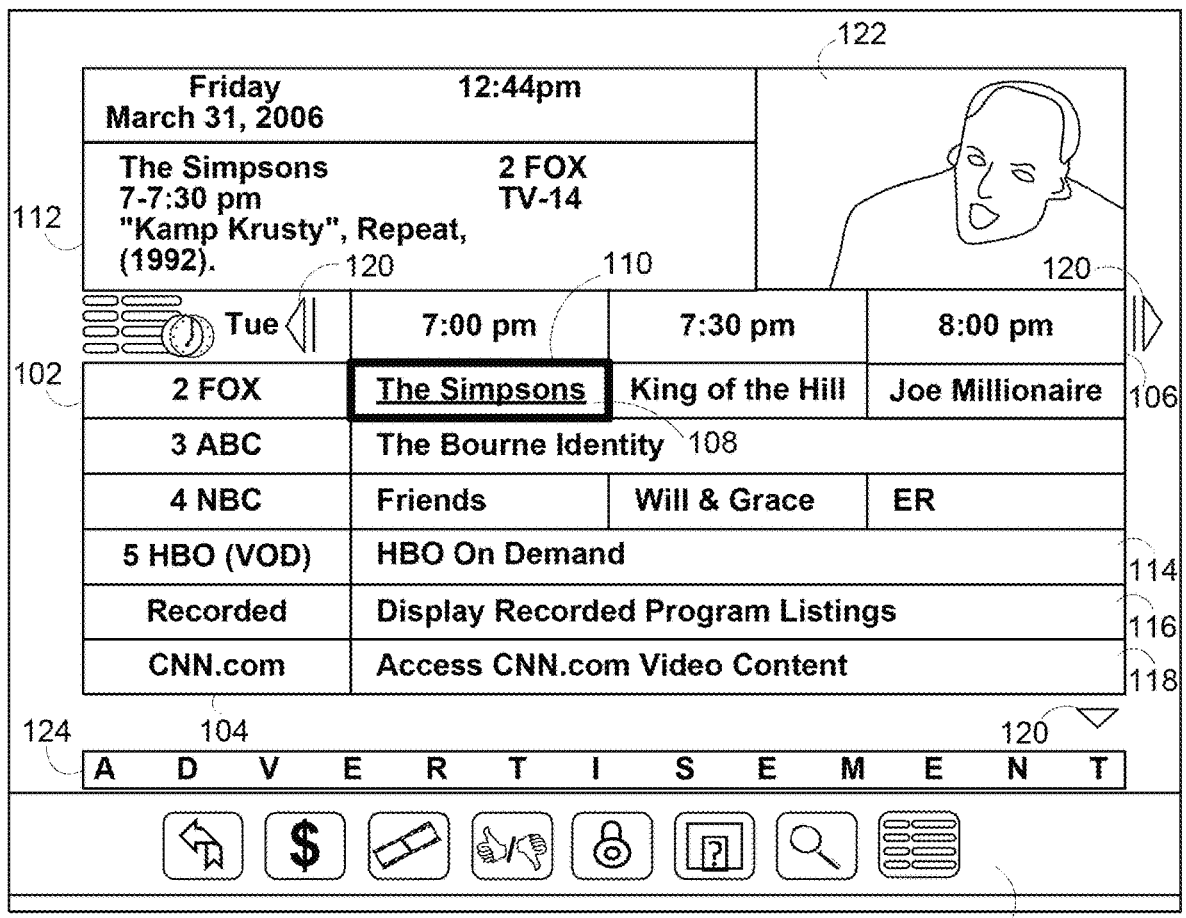
FIG. 1A shows an illustrative media guidance application for selecting media assets in accordance with some embodiments of the disclosure.

Method and systems are disclosed herein for a media guidance application configured to monitor brain activity. As the amount of content available to users in any given content delivery system can be substantial, many users desire a form of media guidance through an interface that allows users to efficiently navigate content selections and easily identify content that they may desire. An application that provides such guidance is referred to herein as an interactive media guidance application or, sometimes, a media guidance application or a guidance application.

Interactive media guidance applications may take various forms depending on the content for which they provide guidance. One typical type of media guidance application is an interactive television program guide. Interactive television program guides (sometimes referred to as electronic program guides) are well-known guidance applications that, among other things, allow users to navigate among and locate many types of content or media assets. Interactive media guidance applications may generate graphical user interface screens that enable a user to navigate among, locate and select content. As referred to herein, the terms "media asset" and "content" should be understood to mean an electronically consumable user asset, such as television programming, as well as pay-per-view programs, on-demand programs (as in video-on-demand (VOD) systems), Internet content (e.g., streaming content, downloadable content, Webcasts, etc.), video clips, audio, content information, pictures, rotating images, documents, playlists, websites, articles, books, electronic books, blogs, advertisements, chat sessions, social media, applications, games, and/or any other media or multimedia and/or combination of the same. Guidance applications also allow users to navigate among and locate content. As referred to herein, the term "multimedia" should be understood to mean content that utilizes at least two different content forms described above, for example, text, audio, images, video, or interactivity content forms. Content may be recorded, played, displayed or accessed by user equipment devices, but can also be part of a live performance.

With the advent of the Internet, mobile computing, and high-speed wireless networks, users are accessing media on user equipment devices which they traditionally did not use. As referred to herein, the phrase "user equipment device," "user equipment," "user device," "electronic device," "electronic equipment," "media equipment device," or "media device" should be understood to mean any device for accessing the content described above, such as a television, a Smart TV, a set-top box, an integrated receiver decoder (IRD) for handling satellite television, a digital storage device, a digital media receiver (DMR), a digital media adapter (DMA), a streaming media device, a DVD player, a DVD recorder, a connected DVD, a local media server, a BLU-RAY player, a BLU-RAY recorder, a personal computer (PC), a laptop computer, a tablet computer, a WebTV box, a personal computer television (PC/TV), a PC media server, a PC media center, a hand-held computer, a stationary telephone, a personal digital assistant (PDA), a mobile telephone, a portable video player, a portable music player, a portable gaming machine, a smart phone, or any other television equipment, computing equipment, or wireless device, and/or combination of the same. In some embodiments, the user equipment device may have a front facing screen and a rear facing screen, multiple front screens, or multiple angled screens. In some embodiments, the user equipment device may have a front facing camera and/or a rear facing camera.

In some embodiments, the user equipment device may include a smart wearable accessory, a smart headset, or any other suitable wearable accessory that includes brain activity detectors for monitoring the brain of a user. On these user equipment devices, users may be able to navigate among and locate the same content available through a television. Consequently, media guidance may be available on these devices, as well. The guidance provided may be for content available only through a television, for content available only through one or more of other types of user equipment devices, or for content available both through a television and one or more of the other types of user equipment devices. The media guidance applications may be provided as on-line applications (i.e., provided on a web-site), or as stand-alone applications or clients on user equipment devices. Various devices and platforms that may implement media guidance applications are described in more detail below.

In some embodiments, a user device may be configured to monitor brain activity upon which various media guidance application operations and features may be based. For example, based on brain activity information, the media guidance application may recommend media assets that correspond to a mood of a user or are likely to induce a preferred mood of the user, provide on-screen feedback about current brain activity of the user, adjust media assets and/or media guides in order to compensate for unusual brain activity in distinct areas of the brain, adjust power levels in the user device, and/or any combinations thereof. Brain monitoring devices are described in for example, Klappert et al., U.S. patent application Ser. No. 14/038,158, filed Sep. 26, 2013, which is hereby incorporated by reference herein in its entirety.

In some embodiments, the user device may incorporate and/or have access to a brain activity detector such as an electroencephalogram unit ("EEG"). An EEG measures electrical activity associated with a brain of a user. For example, an EEG may measure voltage fluctuations and/or the frequency or frequency range of voltage fluctuations generated by the brain of a user.

For example, an EEG may describe rhythmic brain activity. Rhythmic activity (e.g., activity associated with neural oscillation) also known as brain waves may be described in terms of frequency bands or frequency ranges. For example, a delta band includes a frequency range of up to about 4 Hz. Delta bands are, in some circumstances, associated with a sleeping state of a user. Theta bands include a frequency range of 4 to 8 Hz. Theta bands are, in some circumstances, associated with drowsiness. Alpha bands include a frequency range of 8 to 13 Hz. Alpha bands are, in some circumstances, associated with a relaxed state and/or the blinking of a user's eyes. Beta bands include frequencies of 13 to 30 Hz. Beta bands are, in some circumstances, associated with alertness, concentration, and/or anxiety. Gamma bands include a frequency range of 30 to 100 Hz. Gamma bands are, in some circumstances, associated with combinations of senses of a user (e.g., sight, smell, sound, touch, taste) and/or short term memory. Frequency bands and frequency ranges as well as the symmetry of these bands and ranges across the brain of a user are also associated with various moods, which is discussed in detail in Rybak, "Frontal Alpha Power Asymmetry in Aggressive Children and Adolescents With Mood and Disruptive Behavior Disorders," Clinical EEL and Neuroscience, Vol. 3, 2006, which is hereby incorporated by reference herein in its entirety.

Additional discussion about the use of EEG's to detect a level of attention, engagement, frustration, anxiety, emotional state, and comprehension are discussed in detail in Tan, Bao Hong, "Using a Low-cost EEG Sensor to Detect Mental States, CMU-CS-12-134, School of Computer Science, Carnegie Mellon University, August 2012, Hamadicharef et al., "Learning EEG-based Spectral-Spatial Patterns for Attention Level Measurement," Institute for Infocomm Research, 2009, Bos, Danny Oude, "EEG-based Emotion Recognition, The Influence of Visual and Auditory Stimuli," Department of Computer Science, University of Twente, 2006, and Pradeep et al., U.S. Pat. No. 8,392,250, issued Mar. 5, 2013, which are hereby incorporated by reference herein in their entirety.

In some embodiments, EEG detectors may be placed in reference locations on a cranium defined according to the international 10/20 standard by the American Electroencephalographic Society. Each of the EEG detectors may be positioned at any one of a plurality of reference locations on a cranium that are spaced apart by 10% of the distance of an arc across the cranium. Additional information about the 10/20 system are discussed in detail in the article "10/20, 10/10, and 10/5 systems revisited: Their validity as relative-head-surface-based positioning systems," NeuroImage V35 (2007), page 1600-1611, which is hereby incorporated by reference herein in its entirety.

As described in further detail below in reference to FIG. 6-11, each of the plurality of locations may correspond to a position associated with a brain region (e.g., an occipital lobe, temporal lobe, frontal lobe, parietal lobe, etc.) or a position of a user device associated with controlling particular media guidance application operations. A system may include a database that correlates brain signals to each of the plurality of reference locations. A system may determine a position of a brain activity detector on a user's cranium by cross-referencing a brain signal measured by the brain activity detector with the database. As referred to herein, a "position" refers to a locus or set of loci on a cranium at which a brain activity detector or user device may have been placed. For example, a position may correspond to certain brain portions, or a location at which brain signals having specific characteristics can be measured.

Measurements of a brain signal at a particular one of the plurality of reference locations may provide more information about a brain state corresponding to the brain portion at the location. As referred to herein, "measurement" or "metric" refers to a quantitative (e.g., amplitude, frequency, intensity) or qualitative (e.g., transduced electrical signals from an EEG) value representing a detected brain signal (e.g., an EEG signal or EMG signal). For example, a brain signal measured from a brain activity detector positioned on the occipital lobe may provide more information about vision related brain states (e.g., whether the user is receiving visual stimuli, whether a user is blinking eyes, etc.), than measurements at other positions not corresponding to the occipital lobe. For example, a brain signal measured at a position on the frontal lobe may provide more information about emotion related brain states (e.g., a mood of the user, whether the user is happy, angry, sad, etc.), than measurements at other positions not corresponding to the frontal lobe. For example, a brain signal measured at a position on the temporal lobe may provide more information about hearing related brain states (e.g., whether the user is receiving auditory stimuli), than measurements at other positions not corresponding to the temporal lobe. For example, a brain signal measured at a position on the parietal lobe may provide more information about vision related brain states (e.g., an attention level of the user, whether the user is reading text), than measurements at other positions not corresponding to the parietal lobe.

In some embodiments, the media guidance application provides different sets of media guidance application operations, based on which brain portion the media guidance application is able to measure the brain signals of. For example, the media guidance application may provide channel changing operations based on measurements from the occipital lobe or muscles near the occipital lobe (e.g., determining an eye blink pattern of a user from EEG measurements of the occipital lobe or EMG measurements from muscles near the occipital lobe). For example, the media guidance application may provide a volume changing operation based on measurements from the parietal lobe (e.g., determining a level of attention of the user to a program). For example, the media guidance application may provide program recommendations based on measurements from the frontal lobe (e.g., determining the mood of the user).

In some embodiments, the media guidance application may generate for display messages instructing a user to re-position the brain monitoring user device in order to detect access to certain functions. For example, the media guidance application may generate messages instructing the user that in order to access the channel changing operations, the user device should be positioned so that brain activity detectors on the user device can measure brain signals from the occipital lobe, which provides information on eye blink activity. The user interface for the media guidance application will be discussed further below in reference to FIG. 1B.

As referred to herein, a "brain signal" is any type of signal that may be measured from a user that is indicative of a brain of the user. In some embodiments, the brain signal may include brain wave signals, brain temperature signals, brain blood flow signals, or any other suitable brain signals. For example, brain wave signals or brain wave frequency signals may include EEG signals, EMG signals or any other suitable wave signals. For example, a brain temperature signal may include a measurement of a local temperature of a portion of the brain at a position on the cranium, a measurement of local temperature of the scalp at a position on the cranium, or any other suitable brain temperature signal. A brain blood flow signal may be a measurement of blood flow of a portion of the brain at a position on the cranium, a measurement of a blood flow in scalp at a position on the cranium, or any other suitable blood flow signal. A brain oxygen signal may be a measurement of oxygen content in blood flowing through a portion of the brain at a position on the cranium, a measurement of oxygen content in blood flow in scalp at a position on the cranium, or any other suitable oxygen signal.

It should be noted that any embodiment herein related to triggering media guidance application operations based on brain activity may also be adapted to trigger media guidance application operations based on any biometric measurement (e.g., heart rate, perspiration rate, blood pressure, etc.). Furthermore, any embodiment herein related to triggering media guidance application operations based a position of a user device on the cranium or near the brain of a user may also be adapted to trigger media guidance application operations based on a position relative to any other part of the user's body (e.g., relative to a user's heart, hand, stomach, feet, etc.)

In some embodiments, the user device incorporates and/or has access to an electromyogram unit ("EMG"). An EMG measures the electrical activity of muscles at rest and during contraction. The use of EMG and EEG for providing biofeedback is discussed in detail in Frank et al., "Biofeedback in medicine: who, when, why and how?" Ment. Health Fam. Med., June 2010, and Wartena et al., U.S. Patent Application Publication No. 2012/0029322, filed Mar. 24, 2010, which is hereby incorporated by reference herein in its entirety. In some embodiments, the user device may include additional components for detecting brain activity, moods, and attentiveness of a user as discussed in detail in Lee et al., U.S. Pat. No. 8,332,883, issued Dec. 11, 2012, and Bill, U.S. Pat. No. 8,373,768, issued Feb. 12, 2013, which are hereby incorporated by reference herein in their entirety.

In some embodiments, a user device may also distinguish between the different areas of the brain and the different functions of each area of the brain. For example, the frontal lobes are typically associated with planning, problem-solving, voluntary motor control, cognition, intelligence, attention, language processing and comprehension, and various emotions. The parietal lobe is typically associated with perception and integration of somatosensory information (e.g., touch, pressure, temperature, and pain) visuo-spatial processing, spatial attention, spatial mapping, and number representation. The occipital lobe is typically associated with vision, including color, orientation, and motion. The temporal lobe is typically associated with recognition, perception, hearing, smell, and memory. The regions and functions of the brain, in particular their effect on attention and emotion are discussed in detail in Yamasaki et al., "Dissociable prefrontal brain systems for attention and emotion," PNAS, vol. 99, no. 17, 2002, which is hereby incorporated by reference in its entirety.

In some embodiments, a user device may be configured as a headset. As used herein a "headset" refers to any device or article worn or affixed to a user for monitoring brain activity. For example, a user device for monitoring brain activity may be fashioned as a pair of headphones, a hat, a helmet, a pair of glasses, and/or other configuration for use by a user. In some embodiments, a headset may be powered by a local energy storage device (e.g., a battery). For example, in some embodiments, a headset may be rechargeable and/or include replaceable energy storage devices.

The media guidance application (or a user device upon which the media guidance application is implemented) may manage power consumption of the user device based on brain activity of a user. For example, the media guidance application may operate in a plurality of modes each associated with a power consumption and/or sensitivity level. For example, the media guidance application (or the user device upon which the media guidance application is implemented) may trigger various modes on the user device based on a change (or lack of change during a period of time) in brain activity (e.g., a brain state, frequency range, etc.).

Additionally or alternatively, the media guidance application (or the user device upon which the media guidance application is implemented) may trigger various modes on the user device for detecting brain activity based on the particular media guidance operation being performed (or not being performed). For example, the media guidance application may determine that a particular mode (e.g., with a particular power consumption level and/or sensitivity level) corresponds to determining a mood or a user, whereas a different mode corresponds to determining an attentiveness level of a user.

For example, in response to a user request to perform media guidance operations (e.g., schedule a recording) based on monitored brain activity, the media guidance application may initiate a first mode, and, in response to receiving a user request, to perform a different media guidance operation (e.g., recommend a media listing based on a mood of the user), the media guidance application may initiate a second mode. Furthermore, the media guidance application may automatically adjust the various modes initiated and/or switch from one mode to another. For example, in response to detecting that the brain activity of the user does not correspond to a threshold range of brain activity (e.g., associated with actively performing media guidance application operations), the media guidance application may change from a first mode to the second mode (e.g., associated with non-actively performing media guidance applications). This "sleep" or "stand-by" mode may feature reduced power consumption levels and/or sensitivity levels, which may be beneficial in conserving energy consumption as well as reducing a user's exposure to the techniques used to monitor the brain activity.

For example, the media guidance application (or a user device upon which the media guidance application is implemented) may include a "sleep mode" (e.g., a lower powered/lower sensitivity mode) that is initiated after prolonged periods of similar brain activity and/or repetitive brain activity cycles (e.g., indicating that the user is sleeping, engaged in a repetitive activity, and/or does not currently need to perform any media guidance application operations. For example, the media guidance application may initiate the sleep mode in response to determining that the brain activity of the user has dropped below a first threshold range (e.g., associated with an awake user). In another example, the media guidance application may detect that the brain activity of the user exceeds a second threshold range (e.g., associated with a sleeping user), and in response, initiate an "active mode."

In some embodiments, a media guidance application (or a user device upon which the media guidance application is implemented) may detect and/or monitor brain activity of a user. In some embodiments, the media guidance application may determine whether or not the brain activity of a user corresponds to a threshold range. As referred to herein, a "threshold range" refers to a frequency range, or intensity of amplitudes of components of a frequency range, that defines the boundaries of a brain state. For example, a threshold range may be defined as a particular frequency range (in Hz) associated with a brain state of a user, may be defined as frequency bands associated with a brain state of a user, and/or may be defined according to any other measurement that describes the current, preferred, past, and/or future brain state of a user. In some embodiments, a threshold range may account for any transient variations and amplitudes in brain state. For example, a threshold range may be defined as an average frequency, frequency range, intensity of frequency, intensity of frequency ranges and/or frequency band over a particular period of time.

In some embodiments, a media guidance application may take as input a configuration of a brain monitoring user device. As referred to herein, a "configuration" of a brain monitoring user device refers to a mode or orientation of a user device at a position of the user device, in which particular media guidance application operations may be performed by a user. For example, as discussed further below in reference to FIG. 9, a configuration of the brain monitoring user device may be set by positioning a user device at a particular location on a user or setting a switch on the brain monitoring device or a control device for the brain monitoring user device. For example, a configuration of the brain monitoring user device may be based on how the brain monitoring user device is positioned on a user's cranium. For example, if the user device is a headband (e.g., incorporated into a baseball hat), a first configuration may relate to a user device being positioned such that a front of the headband as at the front of the user's head and a back of the headband is at the back of the user's head, and the headband is level with the user's head. For example, a second configuration may relate to a user device being positioned such that the headband (and the baseball hat) is tilted on the user's head (e.g., a right side of the head band is lower on the user's head than a left side of the head band).

For example, a third configuration may relate to a user device being positioned such that the headband (and the baseball hat) is backwards (relative to the first configuration). Positions and configurations of a user device are discussed further below in reference to FIG. 10.

In some embodiments, the media guidance application may customize or select different media guidance application operations based on the configuration or position of the brain monitoring user device. For example, the configuration of the brain monitoring user device may affect a brain state that can be determined by the media guidance application. For example, eye blink brain states may be determined from the occipital lobe, attention level brain states may be determined from the parietal lobe, and content recommendations may be determined from the frontal lobe. A system may include a database that maps channel changing operations to eye blinking brain states, volume changing operations to attention level brain states, and content recommendations to mood brain states. The system may measure brain signals using a user device and determine which lobes the brain signals are measured from. Based on the lobes from which the brain signals are measured, the system may determine a brain state (e.g., eye blink brain state, attention level brain state, or mood brain state), and provide media guidance application operations corresponding to the determined brain state (e.g., channel changing operations for the eye blink brain state, volume changing operations for the attention level brain state, or content recommendations for the mood brain state).

As referred to herein, a "brain state" refers to a qualitative assessment of the mood, level of anxiety, level of attentiveness, level of comprehension, level of proficiency associated with one or more functions (e.g., reading text on a screen, hearing audio, etc.) of a user, and/or a combination thereof associated with the brain activity of the user. A brain state can be quantified as corresponding to a particular threshold range, and different brain states may be compared based on their corresponding threshold ranges.

Brain states may be identified by a user device (e.g., upon which a media guidance application is implemented) that incorporates and/or have access to a device for monitoring brain waves (e.g., an EEG, EMG, and/or any other device discussed herein). The media guidance application may monitor the brain activity (e.g., brain waves) of a user and determine a first brain state of the user based on the brain activity. The first brain state (e.g., the current frequency range or intensity range of a frequency range of voltage fluctuations in the brain, electrical activity of muscles of the brain at rest and during contraction, and/or threshold range) may correspond to a first mood or level of attentiveness to a certain task (e.g., reading, listening, etc.) of the user.

To determine a mood corresponding to a brain state, the media guidance application may cross-reference data associated with the brain state of the user (e.g., a frequency range, intensity range within a frequency range, an electrical activity of the muscles of the brain, and/or a threshold range) with a database associated with data related to brain states and corresponding moods. For example, based on the cross-reference, the media guidance application may determine that the data associated with the brain state of the user indicates that the user is confused, nervous, etc. The media guidance may then select a new brain state (e.g., corresponding to a preferred mood, attentiveness level, etc.) based on a current time, a user input, a current activity, or a preferred biorhythmic pattern associated with the user.

In some embodiments, a media guidance application may cross-reference brain signals detected from a brain monitoring user device in order to determine a position of the user device. For example, a brain signal may include constituent signals as described further below in the context of FIG. 11. The intensities of the constituent signals may form a distinct pattern that is unique to each position on a user's cranium. A brain signal-locations database may include records that correlate brain signals (e.g., the intensity of constituent signals or sub-band signals) to different locations on a user's cranium, as described further below in the context of FIGS. 7-8. A system may cross-reference a measured brain signal with the database in order to determine a location of a user's cranium at which the measured brain signal might have been measured or detected.

In some embodiments, a media guidance application may determine a brain state or set of candidate brain states based on a position of a brain monitoring user device or positions of brain activity detectors in a brain monitoring user device. For example, a cranium location/brain portion database may store records that correlate positions of a user device or positions of certain brain activity detectors in a user device to certain brain regions, and associated characteristics of the brain regions. As referred to herein, "brain region" and "brain portion" refer to areas of a brain (e.g., the frontal lobe, occipital lobe, parietal lobe, temporal lobe, etc.). For example, a system may determine a position of a brain activity detector (e.g., incorporated into a user device), cross-reference the position of the brain activity detector with the cranium location/brain portion database to determine that the position corresponds to the temporal lobe, and retrieve a set of media guidance application operations that may be controlled using brain signals originating from the temporal lobe.

For example, a media guidance application may determine a set of media guidance application operations to enable or provide to a user based on a position of a user device or positions of brain activity detectors on a user device. For example, a brain portion/operation database may include records that correlate brain portions to sets of media guidance application operations. For example, a system may first determine a position of a brain activity detector, and then determine a brain portion corresponding to the position by cross-referencing the position with the cranium location/brain portion database and the system may then cross-reference the brain portion with the brain portion/operation database. The system may determine that a user device is positioned such that it can detect brain signals from the occipital lobe, and can therefore determine eye blink brain states of a user. The system may then provide a set of channel changing operations, correlated with the eye blink brain state. For example, the system may determine that the user is blinking quickly and change the channel upwards. For example, the system may determine that the user is blinking slowly and change the channel downwards. Although the operations above have been described in a three-step process using three databases, it should be understood that any number of steps or databases or organizations of databases can be used.

To select a media asset for display, the media guidance application may cross-reference a preferred brain state with a database that includes a plurality of previous brain states of the user (e.g., representing various moods, attentiveness levels, etc.) and corresponding categories of media assets that the user was consuming during each of the previous brain states. In response to determining a media asset is of the category of media assets that the user was consuming during a previous brain state corresponding to the second brain state, the media guidance application selects the media asset for display to the user.

The media guidance application may also calibrate and/or perform a training/set-up mode. For example, the media guidance application may receive information from the user, in which the user describes (or names) a current position and/or configuration of a user device. In some embodiments, the media guidance application may generate for display a message to the user, instructing the user to re-position a brain-monitoring user device on the cranium of the user in order to better detect brain signals (or to access particular media guidance application operations). For example, the media guidance application may generate for display a message to the user instructing the user to re-position the brain monitoring user device in order to access different sets of media guidance application operations related to different brain regions. For example, the media guidance application may instruct the user to re-position the brain monitoring user device such that brain activity detectors are positioned on the occipital lobe in order to access media guidance application operations related to channel changing (and triggered by brain signals originating from the occipital lobe).

The media guidance application may perform numerous operations for the user. As referred to herein, a "media guidance application operation" refers to any operation or function corresponding to providing, receiving, and generating media guidance data for consumption by a user. For example, media guidance application operations include displaying media guidance data, providing options to navigate, select, and edit media guidance data or content (e.g., a media asset) associated with media guidance data, and/or manipulating a device used to access (e.g., a display device), retrieve (e.g., a server), and/or associate media guidance data with a user (e.g., a user device for monitoring brain activity). One of the operations of the media guidance application is to provide media guidance data to users. As referred to herein, the phrase, "media guidance data" or "guidance data" should be understood to mean any data related to content, such as media listings, media-related information (e.g., broadcast times, broadcast channels, titles, descriptions, ratings information (e.g., parental control ratings, critic's ratings, etc.), genre or category information, actor information, logo data for broadcasters' or providers' logos, etc.), media format (e.g., standard definition, high definition, 3D, etc.), advertisement information (e.g., text, images, media clips, etc.), on-demand information, blogs, websites, and any other type of guidance data that is helpful for a user to navigate among and locate desired content selections.

Other operations of a media guidance application are to play media assets and provide fast access playback operations for those media assets. As referred to herein, the phrase "fast-access playback operations" should be understood to mean any operation that pertains to playing back a non-linear media asset faster than normal playback speed or in a different order than the media asset is designed to be played, such as a fast-forward, rewind, skip, chapter selection, segment selection, skip segment, jump segment, next segment, previous segment, skip advertisement or commercial, next chapter, previous chapter or any other operation that does not play back the media asset at normal playback speed. The fast-access playback operation may be any playback operation that is not "play," where the play operation plays back the media asset at normal playback speed.

FIGS. 1A-C and 2 show illustrative display screens that may be used to provide media guidance data. The display screens shown in FIGS. 1A-C and 2 may be implemented on any suitable user equipment device or platform. While the displays of FIGS. 1A-C and 2 are illustrated as full screen displays, they may also be fully or partially overlaid over content being displayed. A user may indicate a desire to access content information by selecting a selectable option provided in a display screen (e.g., a menu option, a listings option, an icon, a hyperlink, etc.) or pressing a dedicated button (e.g., a GUIDE button) on a remote control or other user input interface or device. In response to the user's indication, the media guidance application may provide a display screen with media guidance data organized in one of several ways, such as by time and channel in a grid, by time, by channel, by source, by content type, by category (e.g., movies, sports, news, children, or other categories of programming), or other predefined, user-defined, or other organization criteria. The organization of the media guidance data is determined by guidance application data. As referred to herein, the phrase, "guidance application data" should be understood to mean data used in operating the guidance application, such as program information, guidance application settings, user preferences, or user profile information.

FIG. 1A shows illustrative grid program listings display 100 arranged by time and channel that also enables access to different types of content in a single display. Display 100 may include grid 102 with: (1) a column of channel/content type identifiers 104, where each channel/content type identifier (which is a cell in the column) identifies a different channel or content type available; and (2) a row of time identifiers 106, where each time identifier (which is a cell in the row) identifies a time block of programming. Grid 102 also includes cells of program listings, such as program listing 108, where each listing provides the title of the program provided on the listing's associated channel and time. With a user input device, a user can select program listings by moving highlight region 110. Information relating to the program listing selected by highlight region 110 may be provided in program information region 112. Region 112 may include, for example, the program title, the program description, the time the program is provided (if applicable), the channel the program is on (if applicable), the program's rating, and other desired information.

In addition to providing access to linear programming (e.g., content that is scheduled to be transmitted to a plurality of user equipment devices at a predetermined time and is provided according to a schedule), the media guidance application also provides access to non-linear programming (e.g., content accessible to a user equipment device at any time and is not provided according to a schedule). Non-linear programming may include content from different content sources including on-demand content (e.g., VOD), Internet content (e.g., streaming media, downloadable media, etc.), locally stored content (e.g., content stored on any user equipment device described above or other storage device), or other time-independent content. On-demand content may include movies or any other content provided by a particular content provider (e.g., HBO On Demand providing "The Sopranos" and "Curb Your Enthusiasm"). HBO ON DEMAND is a service mark owned by Time Warner Company L. P. et al. and THE SOPRANOS and CURB YOUR ENTHUSIASM are trademarks owned by the Home Box Office, Inc. Internet content may include web events, such as a chat session or Webcast, or content available on-demand as streaming content or downloadable content through an Internet web site or other Internet access (e.g., FTP).

Grid 102 may provide media guidance data for non-linear programming including on-demand listing 114, recorded content listing 116, and Internet content listing 118. A display combining media guidance data for content from different types of content sources is sometimes referred to as a "mixed-media" display. Various permutations of the types of media guidance data that may be displayed that are different than display 100 may be based on user selection or guidance application definition (e.g., a display of only recorded and broadcast listings, only on-demand and broadcast listings, etc.). As illustrated, listings 114, 116, and 118 are shown as spanning the entire time block displayed in grid 102 to indicate that selection of these listings may provide access to a display dedicated to on-demand listings, recorded listings, or Internet listings, respectively. In some embodiments, listings for these content types may be included directly in grid 102. Additional media guidance data may be displayed in response to the user selecting one of the navigational icons 120. (Pressing an arrow key on a user input device may affect the display in a similar manner as selecting navigational icons 120.)

Display 100 may also include video region 122, advertisement 124, and options region 126. Video region 122 may allow the user to view and/or preview programs that are currently available, will be available, or were available to the user. The content of video region 122 may correspond to, or be independent from, one of the listings displayed in grid 102. Grid displays including a video region are sometimes referred to as picture-in-guide (PIG) displays. PIG displays and their functionalities are described in greater detail in Satterfield et al. U.S. Pat. No. 6,564,378, issued May 13, 2003 and Yuen et al. U.S. Pat. No. 6,239,794, issued May 29, 2001, which are hereby incorporated by reference herein in their entireties. PIG displays may be included in other media guidance application display screens of the embodiments described herein.

Advertisement 124 may provide an advertisement for content that, depending on a viewer's access rights (e.g., for subscription programming), is currently available for viewing, will be available for viewing in the future, or may never become available for viewing, and may correspond to or be unrelated to one or more of the content listings in grid 102. Advertisement 124 may also be for products or services related or unrelated to the content displayed in grid 102. Advertisement 124 may be selectable and provide further information about content, provide information about a product or a service, enable purchasing of content, a product, or a service, provide content relating to the advertisement, etc. Advertisement 124 may be targeted based on a user's profile/preferences, monitored user activity, the type of display provided, or on other suitable targeted advertisement bases.

While advertisement 124 is shown as rectangular or banner shaped, advertisements may be provided in any suitable size, shape, and location in a guidance application display. For example, advertisement 124 may be provided as a rectangular shape that is horizontally adjacent to grid 102. This is sometimes referred to as a panel advertisement. In addition, advertisements may be overlaid over content or a guidance application display or embedded within a display. Advertisements may also include text, images, rotating images, video clips, or other types of content described above. Advertisements may be stored in a user equipment device having a guidance application, in a database connected to the user equipment, in a remote location (including streaming media servers), or on other storage means, or a combination of these locations. Providing advertisements in a media guidance application is discussed in greater detail in, for example, Knudson et al., U.S. Patent Application Publication No. 2003/0110499, filed Jan. 17, 2003; Ward, III et al. U.S. Pat. No. 6,756,997, issued Jun. 29, 2004; and Schein et al. U.S. Pat. No. 6,388,714, issued May 14, 2002, which are hereby incorporated by reference herein in their entireties. It will be appreciated that advertisements may be included in other media guidance application display screens of the embodiments described herein.

Options region 126 may allow the user to access different types of content, media guidance application displays, and/or media guidance application features. Options region 126 may be part of display 100 (and other display screens described herein), or may be invoked by a user by selecting an on-screen option or pressing a dedicated or assignable button on a user input device. The selectable options within options region 126 may concern features related to program listings in grid 102 or may include options available from a main menu display. Features related to program listings may include searching for other air times or ways of receiving a program, recording a program, enabling series recording of a program, setting program and/or channel as a favorite, purchasing a program, or other features. Options available from a main menu display may include search options, VOD options, parental control options, Internet options, cloud-based options, device synchronization options, second screen device options, options to access various types of media guidance data displays, options to subscribe to a premium service, options to edit a user's profile, options to access a browse overlay, or other options.

The media guidance application may be personalized based on a user's preferences. A personalized media guidance application allows a user to customize displays and features to create a personalized "experience" with the media guidance application. This personalized experience may be created by allowing a user to input these customizations and/or by the media guidance application monitoring user activity to determine various user preferences. Users may access their personalized guidance application by logging in or otherwise identifying themselves to the guidance application. Customization of the media guidance application may be made in accordance with a user profile. The customizations may include varying presentation schemes (e.g., color scheme of displays, font size of text, etc.), aspects of content listings displayed (e.g., only HDTV or only 3D programming, user-specified broadcast channels based on favorite channel selections, re-ordering the display of channels, recommended content, etc.), desired recording features (e.g., recording or series recordings for particular users, recording quality, etc.), parental control settings, customized presentation of Internet content (e.g., presentation of social media content, e-mail, electronically delivered articles, etc.) and other desired customizations.

The media guidance application may allow a user to provide user profile information or may automatically compile user profile information. The media guidance application may, for example, monitor the content the user accesses and/or other interactions the user may have with the guidance application. Additionally, the media guidance application may obtain all or part of other user profiles that are related to a particular user (e.g., from other web sites on the Internet the user accesses, such as www.allrovi.com, from other media guidance applications the user accesses, from other interactive applications the user accesses, from another user equipment device of the user, etc.), and/or obtain information about the user from other sources that the media guidance application may access. As a result, a user can be provided with a unified guidance application experience across the user's different user equipment devices. This type of user experience is described in greater detail below in connection with FIG. 4. Additional personalized media guidance application features are described in greater detail in Ellis et al., U.S. Patent Application Publication No. 2005/0251827, filed Jul. 11, 2005, Boyer et al., U.S. Pat. No. 7,165,098, issued Jan. 16, 2007, and Ellis et al., U.S. Patent Application Publication No. 2002/0174430, filed Feb. 21, 2002, which are hereby incorporated by reference herein in their entireties.

In some embodiments, user profile information may be gathered based on brain signals or brain states monitored using a brain monitoring user device. For example, the media guidance application may determine an attention level brain state while a user is watching a program. The media guidance application may determine that a user has higher attention when watching sports programs and update the user profile accordingly.

Figure 1B:
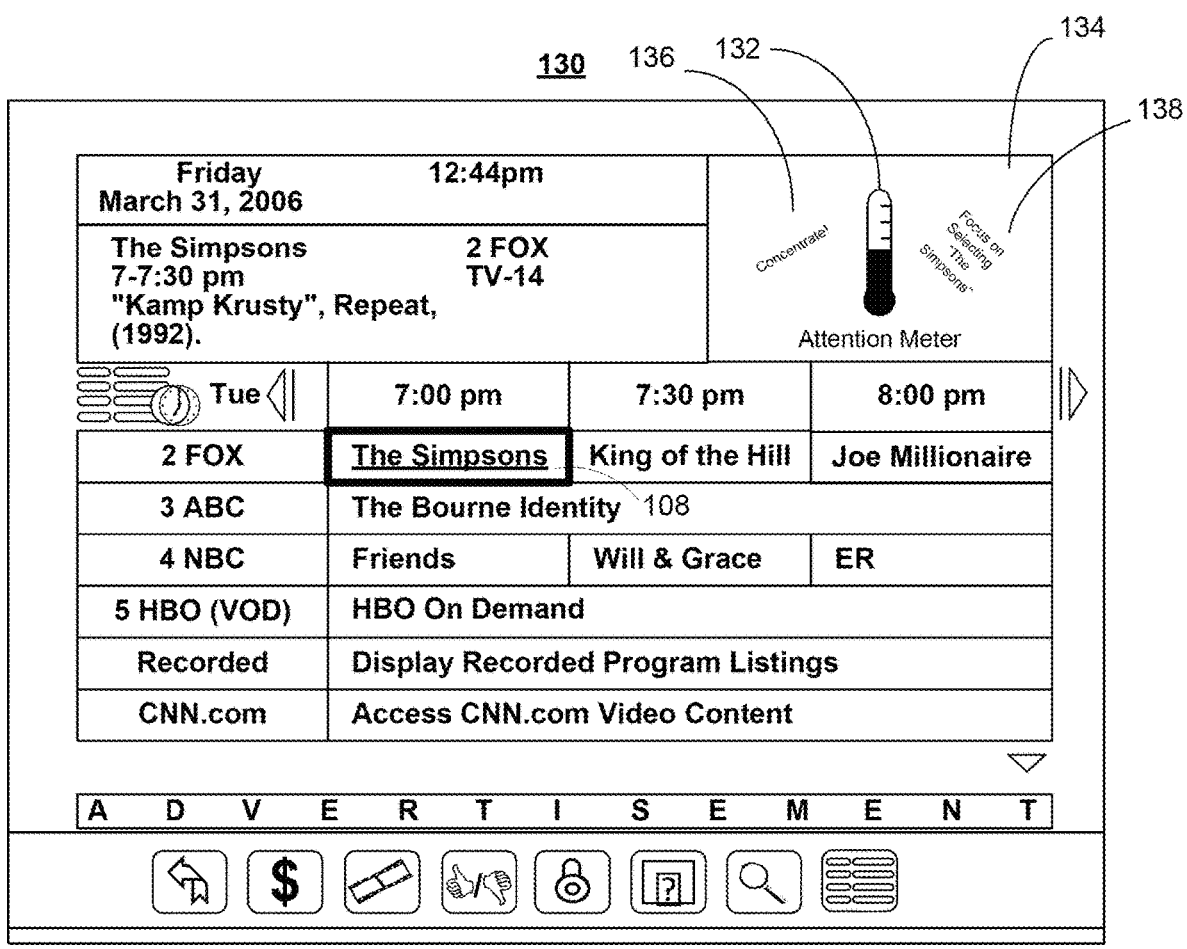
FIG. 1B shows an illustrative media guidance application for selecting media assets featuring an on-screen icon associated with brain activity of a user in accordance with some embodiments of the disclosure.

FIG. 1B shows an illustrative media guidance application for selecting media assets featuring an on-screen icon associated with brain activity of a user. For example, in some embodiments, the media guidance application may generate a display of an on-screen icon that provides feedback to a user regarding the user's current brain activity.

For example, in order to provide a user with guidance related to performing media guidance application operations using their brain waves, the media guidance application may provide a user feedback associated with his/her brain activity. For example, the media guidance application may generate audio/visual cues related to a current brain state of the user and/or preferred brain state (or progress towards a preferred brain state) of the user. For example, the media guidance application may monitor the brain activity of the user associated with a first brain state that is associated with performing a first operation of the media guidance application (e.g., navigating about, or accessing a menu in, a media guide, selecting a media listing, performing a fast-access playback operation, etc.). The media guidance application may generate for display an icon on a display screen that provides feedback to the user related to achieving the first brain state, and in response to detecting a change in the brain activity of the user, the media guidance application may adjust the icon on the display screen to reflect the change in the brain activity of the user.

The icon may include a graphical representation of the brain activity associated with a brain state of the user (e.g., a graph indicating a current attentiveness level associated with a user). and a graphical representation indicating the user's progress towards the first brain state (e.g., a graph indicting an attentiveness level goal and a user's current progress towards that goal). Additionally or alternatively, the icon may include textual information (e.g., descriptions of media guidance applications that may be performed and the brain states needed to trigger each operation) and/or instructions (e.g., instructions on how to achieve a particular brain state).

The media guidance application may also prompt the user to change a position of the brain monitoring user device in order to enable different features. For example, the media guidance application may generate for display a screen that includes any the illustrations in FIGS. 7-10 that show locations on a user's cranium, or positions of a user device on the user's cranium. For example, if the user device is a headband, the media guidance application may generate for display a screen that illustrates how to position the headband on the cranium of the user, as shown in configuration 1010 of FIG. 10. As will be discussed in more detail with respect to FIGS. 6-8 and 10 further below, the position of a user device can affect the brain signals or brain regions, that are detected from a user, and accordingly the brain activity or brain states that can be monitored from a user.

In FIG. 1B, the media guidance application has currently generated a display of icon 134 on display 130. Icon 134 has several graphical representations. For example, icon 134 includes graphical representation 132 of an "Attention Meter," which indicates a current attentiveness level of the user. The "Attention Meter" appears as a thermometer, which when full (e.g., representing a particular threshold level of attentiveness) may trigger a particular media guidance application operation.

As used herein, a "threshold attentiveness level" refers to a particular attentiveness level required for the media guidance application to perform an operation. For example, in response to detecting that the current attentiveness level of a user exceeds the threshold attentiveness level, the media guidance application may perform a particular media guidance application operation (e.g., generated a display of a currently highlighted program).

The use of a graphical and/or animated representation in icon 134 provides an intuitive system through which to provide feedback to a user regarding the brain activity of the user. Additionally or alternatively, the media guidance application may generate other graphical representation in the form of any element that conveys a particular message to a user (e.g., whether a graph, video clip, inspiration message, etc.).

Icon 134 also includes several graphical representations that are textual elements. The graphical representations may serve multiple purposes. For example, while an animated meter may provide a user with his/her current progress related to performing one or more media guidance application operations, textual elements may provide a user instructions for performing a media guidance application operations (e.g., what brain state is needed to trigger the media guidance application operation) and/or indications of what media guidance application operations are available. For example, icon 134 includes a textual element 136 of "Concentrate!" that indicates to a user that the user needs to concentrate (e.g., increase his/her attentiveness level) to perform a particular media guidance application operation.

In addition, icon 134 includes textual element 138, which indicates to the user a particular media guidance application operation that is available. Textual element 138 states, "Focus on Selecting 'The Simpsons'". For example, the media guidance application may respond to detecting a threshold attentiveness level of the user by selecting a currently highlighted object (e.g., program listing 108); therefore, the media guidance application may provide textual element 138 to inform the user of the result of his/her attentiveness level.

In some embodiments, icon 134 may also indicate media guidance application operations that may occur in response to not detecting a particular brain state. For example, if the user does not achieve a brain state corresponding to a level of attentiveness that exceeds a threshold attentiveness level, the media guidance application may automatically perform a particular media guidance application operation.

Figure 1C:
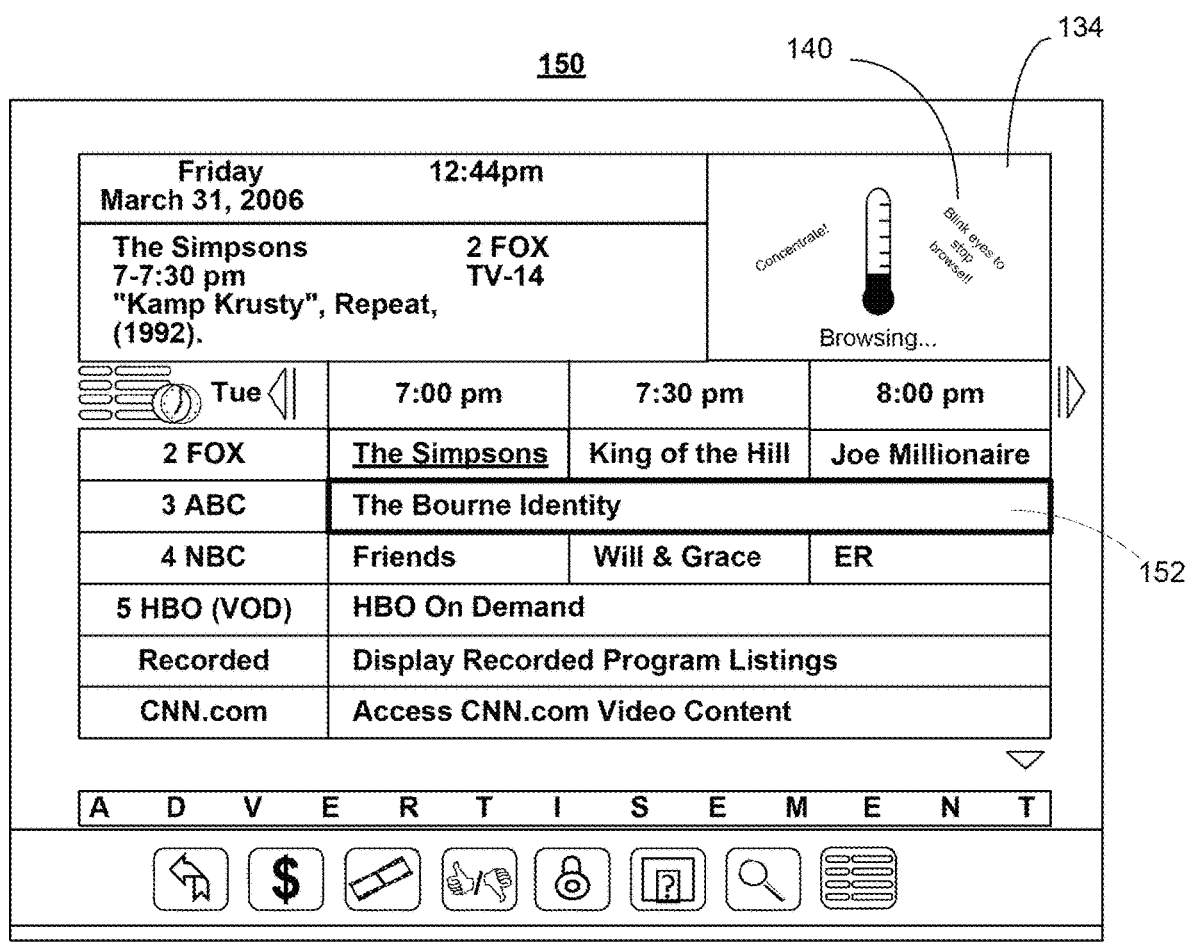
FIG. 1C shows an illustrative media guidance application for selecting media assets featuring an on-screen icon indicating a user currently has a low attentiveness level in accordance with some embodiments of the disclosure.

For example, FIG. 1C shows an illustrative media guidance application for selecting media assets featuring an on-screen icon indicating a user currently has a low attentiveness level. In FIG. 1C, a user did not achieve a threshold attentiveness level (e.g., in a particular time period), and in response, the media guidance application has automatically, without user input, performed a browse operation (e.g., the browse operation may include scrolling from one program listing to another program listing in a media guide, scrolling from one time/date to a different time/date, etc.). As shown in display 150, the media guidance application has initiated a browse operation and program listing 152 is now highlighted.

In display 150, icon 134 now includes new graphical representations that correspond to the media guidance application operation currently being performed. For example, the media guidance applications has now generated a display of icon 134 which includes textual element 140 that instructs a user to "Blink eyes to stop browsing!!" Consequently, in some embodiments, in response to detecting brain activity associated with a user blinking his/her eyes, the media guidance application may halt the browse operation (e.g., the media guidance application may stop scrolling through media listings and remain on a single media listing).

Figure 2:
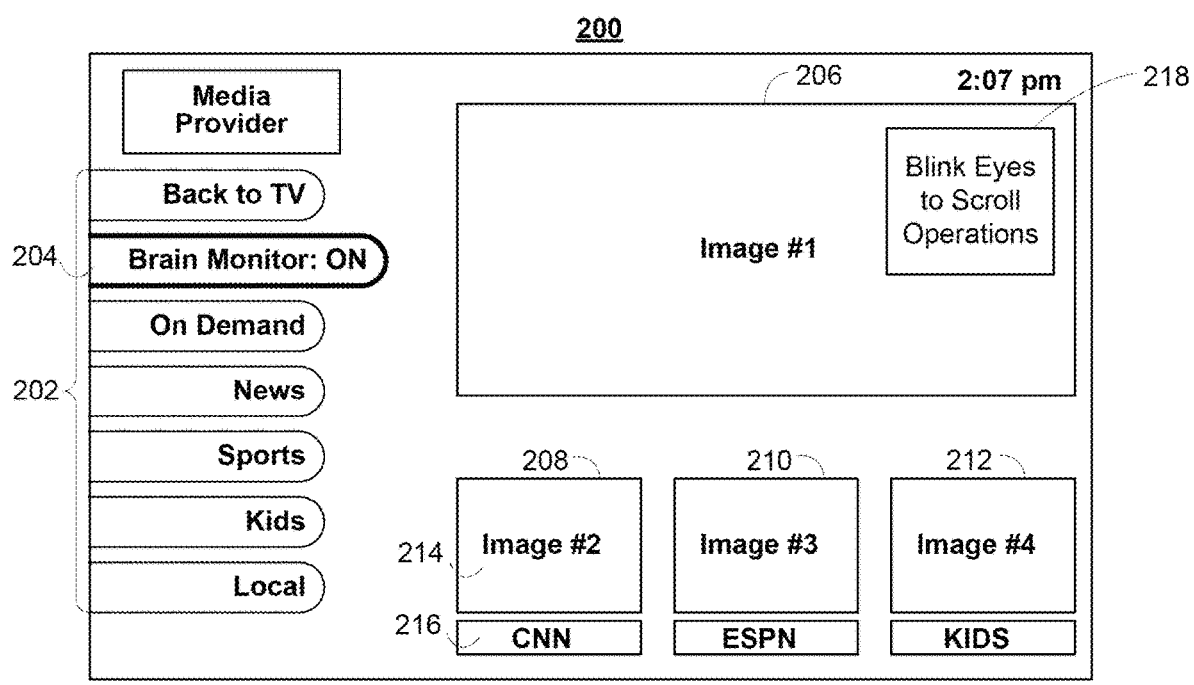
FIG. 2 shows an illustrative media guidance application that may be used to adjust user settings in accordance with some embodiments of the disclosure.

Another display arrangement for providing media guidance is shown in FIG. 2. Video mosaic display 200 includes selectable options 202 for content information organized based on content type, genre, and/or other organization criteria. In display 200, selectable option 204 is selected, thus initiating brain monitoring of a user. In some embodiments, selecting selectable option 204 may switch a user device configured to monitor the brain activity of a user from a first mode (e.g., a "sleep mode") to a second mode (e.g., an "active mode").

In response to selectable option 204 being selected, the media guidance application has also generated a display of icon 218, which instructs a user regarding the monitoring of brain activity. For example, icon 218 instructs a user to blink his/her eyes in order to scroll the different media guidance application operations that are available. For example, the media guidance application may scroll all available media guidance application operations, select a particular operation to monitor for, etc. based on receiving a corresponding eye blink pattern from a user.

As used herein, an "eye blink pattern" refers to a combination of blinks of a user and pauses before or after a blink that causes the media guidance application to perform an action. For example, the media guidance application may be configured to respond to particular eye blink patterns, which may be detected while monitoring brain activity. For example, the media guidance application may monitor alpha bands (e.g., typically associated with eye blinking) in the globus pallidus of the basal ganglia (e.g., the area of the brain typically associated with controlling eye blinking) of a user in order to detect an eye blink pattern. It should be noted that in some embodiments, an eye blink pattern may include only a single blink. Furthermore, the media guidance application may request a user to position the user device or put the user device in a configuration in which brain activity detectors in the user device can adequately receive signals from the globus pallidus, if the user wishes to access media guidance application operations triggered by eye blink patterns.

In display 200 listings may provide graphical images including cover art, still images from the content, video clip previews, live video from the content, or other types of content that indicate to a user the content being described by the media guidance data in the listing. Each of the graphical listings may also be accompanied by text to provide further information about the content associated with the listing. For example, listings 208, 210, and 212 may include more than one portion, including media portion 214 and text portion 216. Media portion 214 and/or text portion 216 may be selectable to view content in full-screen or to view information related to the content displayed in media portion 214 (e.g., to view listings for the channel that the video is displayed on).

The listings in display 200 are of different sizes (i.e., listing 206 is larger than listings 208, 210, and 212), but if desired, all the listings may be the same size. Listings may be of different sizes or graphically accentuated to indicate degrees of interest to the user or to emphasize certain content, as desired by the content provider or based on user preferences. Various systems and methods for graphically accentuating content listings are discussed in, for example, Yates, U.S. Patent Application Publication No. 2010/0153885, filed Dec. 29, 2005, which is hereby incorporated by reference herein in its entirety.

In some embodiments, the listings may be selected based on the brain state of the user, as monitored by a user device and determined by the system. For example, the system may determine that the user device is positioned so that brain signals are measured from the frontal lobe. The system may determine a mood of the user, based on the measured brain signals. For example, the system may determine that that the user is happy and select program listings related to programs in the comedy genre, associated with happy moods, to the user.

Figure 3:
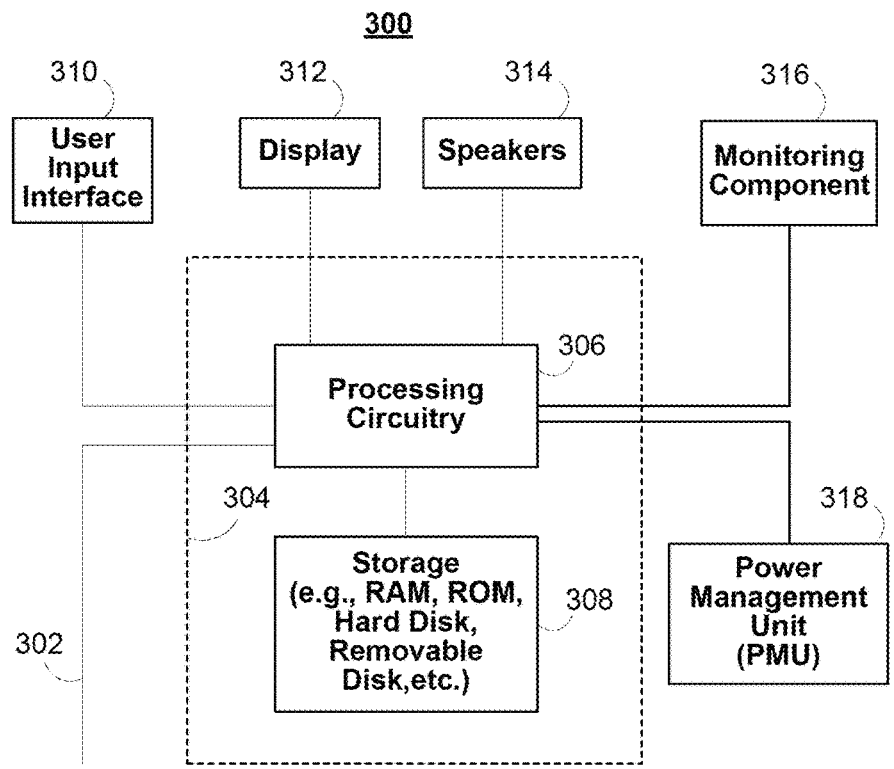
FIG. 3 is a block diagram of an illustrative user equipment device in accordance with some embodiments of the disclosure.

Users may access content and the media guidance application (and its display screens described above and below) from one or more of their user equipment devices. FIG. 3 shows a generalized embodiment of illustrative user equipment device 300. More specific implementations of user equipment devices are discussed below in connection with FIG. 4. User equipment device 300 may receive content and data via input/output (hereinafter "I/O") path 302. I/O path 302 may provide content (e.g., broadcast programming, on-demand programming, Internet content, content available over a local area network (LAN) or wide area network (WAN), and/or other content) and data to control circuitry 304, which includes processing circuitry 306 and storage 308. Control circuitry 304 may be used to send and receive commands, requests, and other suitable data using I/O path 302. I/O path 302 may connect control circuitry 304 (and specifically processing circuitry 306) to one or more communications paths (described below). I/O functions may be provided by one or more of these communications paths, but are shown as a single path in FIG. 3 to avoid overcomplicating the drawing.

Control circuitry 304 may be based on any suitable processing circuitry such as processing circuitry 306. As referred to herein, processing circuitry should be understood to mean circuitry based on one or more microprocessors, microcontrollers, digital signal processors, programmable logic devices, field-programmable gate arrays (FPGAs), application-specific integrated circuits (ASICs), etc., and may include a multi-core processor (e.g., dual-core, quad-core, hexa-core, or any suitable number of cores) or supercomputer. In some embodiments, processing circuitry may be distributed across multiple separate processors or processing units, for example, multiple of the same type of processing units (e.g., two Intel Core i7 processors) or multiple different processors (e.g., an Intel Core i5 processor and an Intel Core i7 processor). In some embodiments, control circuitry 304 executes instructions for a media guidance application stored in memory (i.e., storage 308). Specifically, control circuitry 304 may be instructed by the media guidance application to perform the functions discussed above and below. For example, the media guidance application may provide instructions to control circuitry 304 to generate the media guidance displays. In some implementations, any action performed by control circuitry 304 may be based on instructions received from the media guidance application.

In client-server based embodiments, control circuitry 304 may include communications circuitry suitable for communicating with a guidance application server or other networks or servers. The instructions for carrying out the above mentioned functionality may be stored on the guidance application server. Communications circuitry may include a cable modem, an integrated services digital network (ISDN) modem, a digital subscriber line (DSL) modem, a telephone modem, Ethernet card, or a wireless modem for communications with other equipment, or any other suitable communications circuitry. Such communications may involve the Internet or any other suitable communications networks or paths (which is described in more detail in connection with FIG. 4). In addition, communications circuitry may include circuitry that enables peer-to-peer communication of user equipment devices, or communication of user equipment devices in locations remote from each other (described in more detail below).

Memory may be an electronic storage device provided as storage 308 that is part of control circuitry 304. As referred to herein, the phrase "electronic storage device" or "storage device" should be understood to mean any device for storing electronic data, computer software, or firmware, such as random-access memory, read-only memory, hard drives, optical drives, digital video disc (DVD) recorders, compact disc (CD) recorders, BLU-RAY disc (BD) recorders, BLU-RAY 3D disc recorders, digital video recorders (DVR, sometimes called a personal video recorder, or PVR), solid state devices, quantum storage devices, gaming consoles, gaming media, or any other suitable fixed or removable storage devices, and/or any combination of the same. Storage 308 may be used to store various types of content described herein as well as media guidance information, described above, and guidance application data, described above. Nonvolatile memory may also be used (e.g., to launch a boot-up routine and other instructions). Cloud-based storage, described in relation to FIG. 4, may be used to supplement storage 308 or instead of storage 308.

Control circuitry 304 may include video generating circuitry and tuning circuitry, such as one or more analog tuners, one or more MPEG-2 decoders or other digital decoding circuitry, high-definition tuners, or any other suitable tuning or video circuits or combinations of such circuits. Encoding circuitry (e.g., for converting over-the-air, analog, or digital signals to MPEG signals for storage) may also be provided. Control circuitry 304 may also include scaler circuitry for upconverting and downconverting content into the preferred output format of the user equipment 300. Circuitry 304 may also include digital-to-analog converter circuitry and analog-to-digital converter circuitry for converting between digital and analog signals. The tuning and encoding circuitry may be used by the user equipment device to receive and to display, to play, or to record content. The tuning and encoding circuitry may also be used to receive guidance data. The circuitry described herein, including for example, the tuning, video generating, encoding, decoding, encrypting, decrypting, scaler, and analog/digital circuitry, may be implemented using software running on one or more general purpose or specialized processors. Multiple tuners may be provided to handle simultaneous tuning functions or operations (e.g., watch and record functions or operations, picture-in-picture (PIP) functions, multiple-tuner recording, etc.). If storage 308 is provided as a separate device from user equipment 300, the tuning and encoding circuitry (including multiple tuners) may be associated with storage 308.

A user may send instructions to control circuitry 304 using user input interface 310. User input interface 310 may be any suitable user interface, such as a remote control, mouse, trackball, keypad, keyboard, touch screen, touchpad, stylus input, joystick, voice recognition interface, or other user input interfaces. Display 312 may be provided as a stand-alone device or integrated with other elements of user equipment device 300. Display 312 may be one or more of a monitor, a television, a liquid crystal display (LCD) for a mobile device, or any other suitable equipment for displaying visual images. In some embodiments, display 312 may be HDTV-capable. In some embodiments, display 312 may be a 3D display, and the interactive media guidance application and any suitable content may be displayed in 3D. A video card or graphics card may generate the output to the display 312. The video card may offer various functions such as accelerated rendering of 3D scenes and 2D graphics, MPEG-2/MPEG-4 decoding, TV output, or the ability to connect multiple monitors. The video card may be any processing circuitry described above in relation to control circuitry 304. The video card may be integrated with the control circuitry 304. Speakers 314 may be provided as integrated with other elements of user equipment device 300 or may be stand-alone units. The audio component of videos and other content displayed on display 312 may be played through speakers 314. In some embodiments, the audio may be distributed to a receiver (not shown), which processes and outputs the audio via speakers 314.

Control circuitry 304 may also instruct monitoring component 316. Monitoring component 316 may include one or more additional sub-components (e.g., brain activity detectors, additional detectors, an EEG, EMG, etc.) for monitoring or assisting the monitoring of brain activity of a user. Monitoring component 316 may transmit updates (e.g., associated with brain activity) of a user to control circuitry 304. Control circuitry 304 may compare the updates to data related to brain activity (e.g., threshold ranges, frequency ranges, etc.) of the user and/or other users stored on storage 308 (e.g., to determine whether or not the brain activity of the user corresponds to a particular threshold range and/or mood, attentiveness level, etc.).

It should be noted, monitoring component 316 may, in some embodiments, be located on a separate device in communication with the device upon which a media guidance application (and control circuitry 304) is implemented. For example, in some embodiments, monitoring component 316 may communication with device 300 via a communications network (e.g., communications network 414 (FIG. 4)).

Control circuitry 304 may also instruct power management unit (PMU) 318 to switch user equipment device 300 from a first power mode of operation to a second power mode of operation. Alternatively, PMU 318 may receive instructions to perform the switching directly over communications network 414. For example, monitoring component 316 may send PMU 318 a message telling it to switch user equipment device 300 from a first power mode to a second power mode.

As referred to herein, a first power mode may be a low power mode of operation. A first power mode may be understood to be a sleep mode, a standby mode, a power-off mode, a dormant mode, or a low-power mode. A low-power mode may refer to a mode of operation wherein user equipment device 300 has sufficient power to perform basic computation (e.g., compute whether an update should be performed) using processing circuitry 306 but insufficient power to perform more power-intensive tasks such as communicate with remote devices (e.g., media content source 416 (FIG. 4)) over communications network 414 (FIG. 4) and/or have limited capability to identify brain activity. As referred to herein, a second power mode may be a high power mode of operation. A second power mode may be understood to be an awake mode, an active mode, a full-power mode, a high-power mode, or an update mode, where a device operating at a second power mode has sufficient power to provide updates on brain activity of a user sufficient for determining a mood, attentiveness level, etc. A device operating at a second power mode may consume more power than when operating at a first power mode. In some embodiments, device 300 may operate at a third power mode, wherein the power consumed at the third power mode is greater than that consumed at the first power mode but less than that consumed at the second power mode. A third power mode may be an update mode, wherein device 300 operates at enough power to perform updates but not at full-power mode to perform media guidance application operations. A third power mode may also refer to a low-power mode, as described above. All three modes of operation (e.g., first power mode, second power mode, third power mode) may be used interchangeably within the disclosure.

Once user equipment device 300 is switched to a second power mode of operation, control circuitry 304 updates the media guidance application with data from monitoring component 316 and stores the data in storage 308. As referred to herein, switching refers to activating a component of circuitry within user equipment device 300 that corresponds to a desired power mode of operation. Switching may be performed by PMU 318 to switch user equipment device 300 from a first power mode to a second power mode. A first power mode may correspond to a first circuitry component, and a second power mode may correspond to a second circuitry component. As referred to herein, switching from a first power mode to a second power mode involves deactivating the first circuitry component and activating a second circuitry component.

PMU 318 monitors and manages the power consumption of user equipment device 300. PMU 318 may be configured to monitor the current level of power consumption of user equipment device 300 based on device characteristics such as, but are not limited to, battery usage information, screen brightness, screen saver settings, central processing unit (CPU) power usage, graphic processing unit (GPU) power usage, integrated processor power usage, number of applications currently running on user equipment device 300, number and frequency of recordings scheduled to be performed on user equipment device 300, and the current power mode of operation (e.g., first power mode, second power mode) in addition to brain activity. More specifically, PMU 318 monitors the power state of user equipment device 300 to determine when device 300 switches from a first power mode to a second power mode. In some embodiments, PMU 318 may reside on user equipment device 300 as a component of control circuitry 304. In other embodiments, PMU 318 may be a unit that is external to user equipment device 300. In these cases, PMU 318 may communicate with user equipment device 300 by sending and receiving instructions from control circuitry 304.

PMU 318 may perform the switching in response to various conditions, based on instructions from control circuitry 304. In some embodiments, control circuitry 304 may receive an indication to switch user equipment device 300 from a first power mode to a second power mode. For example, control circuitry 304 may receive a request from a user input interface 310 or monitoring component 316 to perform the switching. In another example, control circuitry 304 may receive over communications network 414 (FIG. 4) via path 302 a message from a remote server indicating that user equipment device 300 should be switched to a second power mode of operation. In each of the aforementioned examples, control circuitry 304 may instruct PMU 318 to switch user equipment device 300 to a second power mode of operation in response to the requests and messages received. These messages and/or requests may include a time field which indicates a future time at which control circuitry 304 should switch device 300 to a second power mode to receive updates over network 414 (FIG. 4) and/or perform updates that are stored in storage 308. This time field may set a timer to switch user device 300 to a second power mode at a specified time. The time field may also set a timer to switch user device 300 to a first power mode at a specified time period when no updates will be sent to device 300.

The guidance application may be implemented using any suitable architecture. For example, it may be a stand-alone application wholly implemented on user equipment device 300. In such an approach, instructions of the application are stored locally, and data for use by the application is downloaded on a periodic basis (e.g., from an out-of-band feed, from an Internet resource, or using another suitable approach). In some embodiments, the media guidance application is a client-server based application. Data for use by a thick or thin client implemented on user equipment device 300 is retrieved on-demand by issuing requests to a server remote to the user equipment device 300. In one example of a client-server based guidance application, control circuitry 304 runs a web browser that interprets web pages provided by a remote server.

In some embodiments, the media guidance application is downloaded and interpreted or otherwise run by an interpreter or virtual machine (run by control circuitry 304). In some embodiments, the guidance application may be encoded in the ETV Binary Interchange Format (EBIF), received by control circuitry 304 as part of a suitable feed, and interpreted by a user agent running on control circuitry 304. For example, the guidance application may be an EBIF application. In some embodiments, the guidance application may be defined by a series of JAVA-based files that are received and run by a local virtual machine or other suitable middleware executed by control circuitry 304. In some of such embodiments (e.g., those employing MPEG-2 or other digital media encoding schemes), the guidance application may be, for example, encoded and transmitted in an MPEG-2 object carousel with the MPEG audio and video packets of a program.

Figure 4:
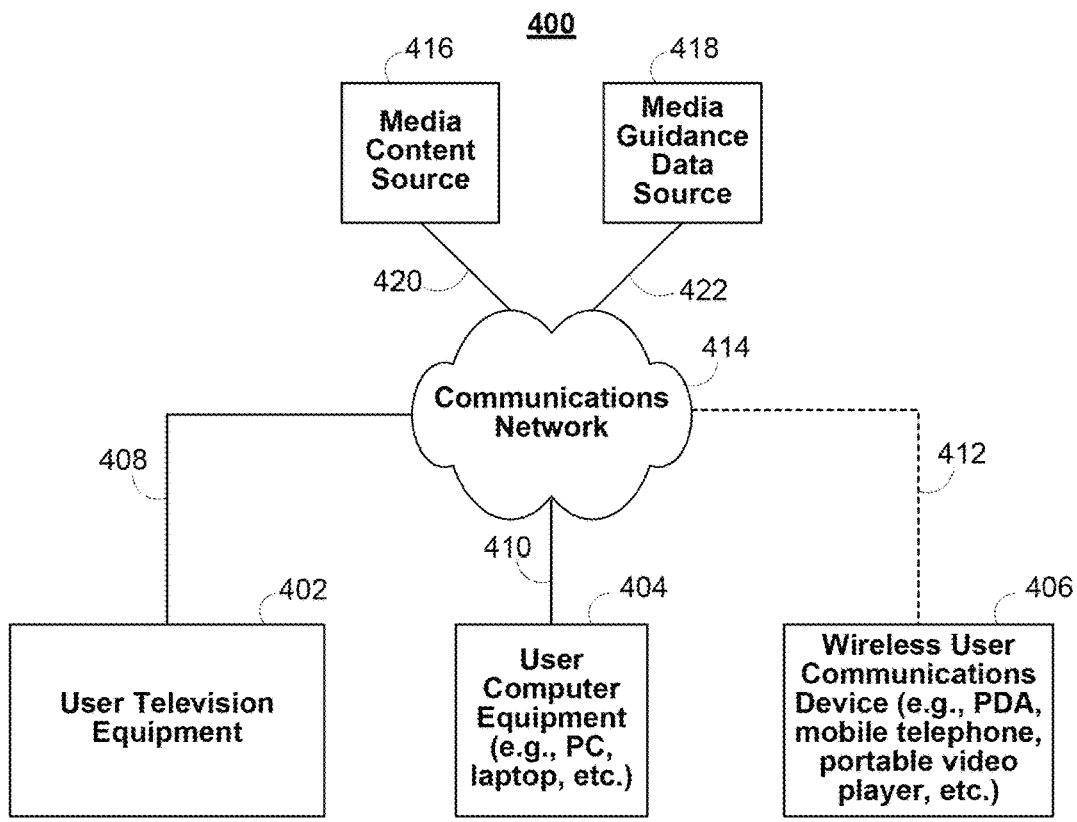
FIG. 4 is a block diagram of an illustrative media system in accordance with some embodiments of the disclosure.

User equipment device 300 of FIG. 3 can be implemented in system 400 of FIG. 4 as user television equipment 402, user computer equipment 404, wireless user communications device 406, or any other type of user equipment suitable for accessing content, such as a non-portable gaming machine. For simplicity, these devices may be referred to herein collectively as user equipment or user equipment devices, and may be substantially similar to user equipment devices described above. User equipment devices, on which a media guidance application may be implemented, may function as a standalone device or may be part of a network of devices. Various network configurations of devices may be implemented and are discussed in more detail below.

A user equipment device utilizing at least some of the system features described above in connection with FIG. 3 may not be classified solely as user television equipment 402, user computer equipment 404, or a wireless user communications device 406. For example, user television equipment 402 may, like some user computer equipment 404, be Internet-enabled allowing for access to Internet content, while user computer equipment 404 may, like some television equipment 402, include a tuner allowing for access to television programming. The media guidance application may have the same layout on various different types of user equipment or may be tailored to the display capabilities of the user equipment. For example, on user computer equipment 404, the guidance application may be provided as a web site accessed by a web browser. In another example, the guidance application may be scaled down for wireless user communications devices 406.

In system 400, there is typically more than one of each type of user equipment device but only one of each is shown in FIG. 4 to avoid overcomplicating the drawing. In addition, each user may utilize more than one type of user equipment device and also more than one of each type of user equipment device.

In some embodiments, a user equipment device (e.g., user television equipment 402, user computer equipment 404, wireless user communications device 406) may be referred to as a "second screen device." For example, a second screen device may supplement content presented on a first user equipment device. The content presented on the second screen device may be any suitable content that supplements the content presented on the first device. In some embodiments, the second screen device provides an interface for adjusting settings and display preferences of the first device. In some embodiments, the second screen device is configured for interacting with other second screen devices or for interacting with a social network. The second screen device can be located in the same room as the first device, a different room from the first device but in the same house or building, or in a different building from the first device.

The user may also set various settings to maintain consistent media guidance application settings across in-home devices and remote devices. Settings include those described herein, as well as channel and program favorites, programming preferences that the guidance application utilizes to make programming recommendations, display preferences, and other desirable guidance settings. For example, if a user sets a channel as a favorite on, for example, the web site www.allrovi.com on their personal computer at their office, the same channel would appear as a favorite on the user's in-home devices (e.g., user television equipment and user computer equipment) as well as the user's mobile devices, if desired. Therefore, changes made on one user equipment device can change the guidance experience on another user equipment device, regardless of whether they are the same or a different type of user equipment device. In addition, the changes made may be based on settings input by a user, as well as user activity monitored by the guidance application.

The user equipment devices may be coupled to communications network 414. Namely, user television equipment 402, user computer equipment 404, and wireless user communications device 406 are coupled to communications network 414 via communications paths 408, 410, and 412, respectively. Communications network 414 may be one or more networks including the Internet, a mobile phone network, mobile voice or data network (e.g., a 4G or LTE network), cable network, public switched telephone network, or other types of communications network or combinations of communications networks. Paths 408, 410, and 412 may separately or together include one or more communications paths, such as, a satellite path, a fiber-optic path, a cable path, a path that supports Internet communications (e.g., IPTV), free-space connections (e.g., for broadcast or other wireless signals), or any other suitable wired or wireless communications path or combination of such paths. Path 412 is drawn with dotted lines to indicate that in the exemplary embodiment shown in FIG. 4 it is a wireless path and paths 408 and 410 are drawn as solid lines to indicate they are wired paths (although these paths may be wireless paths, if desired). Communications with the user equipment devices may be provided by one or more of these communications paths, but are shown as a single path in FIG. 4 to avoid overcomplicating the drawing.

Although communications paths are not drawn between user equipment devices, these devices may communicate directly with each other via communication paths, such as those described above in connection with paths 408, 410, and 412, as well as other short-range point-to-point communication paths, such as USB cables, IEEE 1394 cables, wireless paths (e.g., Bluetooth, infrared, IEEE 802-11x, etc.), or other short-range communication via wired or wireless paths. BLUETOOTH is a certification mark owned by Bluetooth SIG, INC. The user equipment devices may also communicate with each other directly through an indirect path via communications network 414.

System 400 includes content source 416 and media guidance data source 418 coupled to communications network 414 via communication paths 420 and 422, respectively. Paths 420 and 422 may include any of the communication paths described above in connection with paths 408, 410, and 412. Communications with the content source 416 and media guidance data source 418 may be exchanged over one or more communications paths, but are shown as a single path in FIG. 4 to avoid overcomplicating the drawing. In addition, there may be more than one of each of content source 416 and media guidance data source 418, but only one of each is shown in FIG. 4 to avoid overcomplicating the drawing. (The different types of each of these sources are discussed below.) If desired, content source 416 and media guidance data source 418 may be integrated as one source device. Although communications between sources 416 and 418 with user equipment devices 402, 404, and 406 are shown as through communications network 414, in some embodiments, sources 416 and 418 may communicate directly with user equipment devices 402, 404, and 406 via communication paths (not shown) such as those described above in connection with paths 408, 410, and 412.

Content source 416 may include one or more types of content distribution equipment including a television distribution facility, cable system headend, satellite distribution facility, programming sources (e.g., television broadcasters, such as NBC, ABC, HBO, etc.), intermediate distribution facilities and/or servers, Internet providers, on-demand media servers, and other content providers. NBC is a trademark owned by the National Broadcasting Company, Inc., ABC is a trademark owned by the American Broadcasting Company, Inc., and HBO is a trademark owned by the Home Box Office, Inc. Content source 416 may be the originator of content (e.g., a television broadcaster, a Webcast provider, etc.) or may not be the originator of content (e.g., an on-demand content provider, an Internet provider of content of broadcast programs for downloading, etc.). Content source 416 may include cable sources, satellite providers, on-demand providers, Internet providers, over-the-top content providers, or other providers of content. Content source 416 may also include a remote media server used to store different types of content (including video content selected by a user), in a location remote from any of the user equipment devices. Systems and methods for remote storage of content, and providing remotely stored content to user equipment are discussed in greater detail in connection with Ellis et al., U.S. Pat. No. 7,761,892, issued Jul. 20, 2010, which is hereby incorporated by reference herein in its entirety.

Media guidance data source 418 may provide media guidance data, such as the media guidance data described above. Media guidance application data may be provided to the user equipment devices using any suitable approach. In some embodiments, the guidance application may be a stand-alone interactive television program guide that receives program guide data via a data feed (e.g., a continuous feed or trickle feed). Program schedule data and other guidance data may be provided to the user equipment on a television channel sideband, using an in-band digital signal, using an out-of-band digital signal, or by any other suitable data transmission technique. Program schedule data and other media guidance data may be provided to user equipment on multiple analog or digital television channels.

In some embodiments, guidance data from media guidance data source 418 may be provided to users' equipment using a client-server approach. For example, a user equipment device may pull media guidance data from a server, or a server may push media guidance data to a user equipment device. In some embodiments, a guidance application client residing on the user's equipment may initiate sessions with source 418 to obtain guidance data when needed, e.g., when the guidance data is out of date or when the user equipment device receives a request from the user to receive data. Media guidance may be provided to the user equipment with any suitable frequency (e.g., continuously, daily, a user-specified period of time, a system-specified period of time, in response to a request from user equipment, etc.). Media guidance data source 418 may provide user equipment devices 402, 404, and 406 the media guidance application itself or software updates for the media guidance application.

Media guidance applications may be, for example, stand-alone applications implemented on user equipment devices. For example, the media guidance application may be implemented as software or a set of executable instructions which may be stored in storage 308, and executed by control circuitry 304 of a user equipment device 300. In some embodiments, media guidance applications may be client-server applications where only a client application resides on the user equipment device, and server application resides on a remote server. For example, media guidance applications may be implemented partially as a client application on control circuitry 304 of user equipment device 300 and partially on a remote server as a server application (e.g., media guidance data source 418) running on control circuitry of the remote server. When executed by control circuitry of the remote server (such as media guidance data source 418), the media guidance application may instruct the control circuitry to generate the guidance application displays and transmit the generated displays to the user equipment devices. The server application may instruct the control circuitry of the media guidance data source 418 to transmit data for storage on the user equipment. The client application may instruct control circuitry of the receiving user equipment to generate the guidance application displays.

Content and/or media guidance data delivered to user equipment devices 402, 404, and 406 may be over-the-top (OTT) content. OTT content delivery allows Internet-enabled user devices, including any user equipment device described above, to receive content that is transferred over the Internet, including any content described above, in addition to content received over cable or satellite connections. OTT content is delivered via an Internet connection provided by an Internet service provider (ISP), but a third party distributes the content. The ISP may not be responsible for the viewing abilities, copyrights, or redistribution of the content, and may only transfer IP packets provided by the OTT content provider. Examples of OTT content providers include YOUTUBE, NETFLIX, and HULU, which provide audio and video via IP packets. Youtube is a trademark owned by Google Inc., Netflix is a trademark owned by Netflix Inc., and Hulu is a trademark owned by Hulu, LLC. OTT content providers may additionally or alternatively provide media guidance data described above. In addition to content and/or media guidance data, providers of OTT content can distribute media guidance applications (e.g., web-based applications or cloud-based applications), or the content can be displayed by media guidance applications stored on the user equipment device.

Media guidance system 400 is intended to illustrate a number of approaches, or network configurations, by which user equipment devices and sources of content and guidance data may communicate with each other for the purpose of accessing content and providing media guidance. The embodiments described herein may be applied in any one or a subset of these approaches, or in a system employing other approaches for delivering content and providing media guidance. The following four approaches provide specific illustrations of the generalized example of FIG. 4.

In one approach, user equipment devices may communicate with each other within a home network. User equipment devices can communicate with each other directly via short-range point-to-point communication schemes described above, via indirect paths through a hub or other similar device provided on a home network, or via communications network 414. Each of the multiple individuals in a single home may operate different user equipment devices on the home network. As a result, it may be desirable for various media guidance information or settings to be communicated between the different user equipment devices. For example, it may be desirable for users to maintain consistent media guidance application settings on different user equipment devices within a home network, as described in greater detail in Ellis et al., U.S. patent application Ser. No. 11/179,410, filed Jul. 11, 2005. Different types of user equipment devices in a home network may also communicate with each other to transmit content. For example, a user may transmit content from user computer equipment to a portable video player or portable music player.

In a second approach, users may have multiple types of user equipment by which they access content and obtain media guidance. For example, some users may have home networks that are accessed by in-home and mobile devices. Users may control in-home devices via a media guidance application implemented on a remote device. For example, users may access an online media guidance application on a website via a personal computer at their office, or a mobile device such as a PDA or web-enabled mobile telephone. The user may set various settings (e.g., recordings, reminders, or other settings) on the online guidance application to control the user's in-home equipment. The online guide may control the user's equipment directly, or by communicating with a media guidance application on the user's in-home equipment. Various systems and methods for user equipment devices communicating, where the user equipment devices are in locations remote from each other, is discussed in, for example, Ellis et al., U.S. Pat. No. 8,046,801, issued Oct. 25, 2011, which is hereby incorporated by reference herein in its entirety.

In a third approach, users of user equipment devices inside and outside a home can use their media guidance application to communicate directly with content source 416 to access content. Specifically, within a home, users of user television equipment 402 and user computer equipment 404 may access the media guidance application to navigate among and locate desirable content. Users may also access the media guidance application outside of the home using wireless user communications devices 406 to navigate among and locate desirable content.

In a fourth approach, user equipment devices may operate in a cloud computing environment to access cloud services. In a cloud computing environment, various types of computing services for content sharing, storage or distribution (e.g., video sharing sites or social networking sites) are provided by a collection of network-accessible computing and storage resources, referred to as "the cloud." For example, the cloud can include a collection of server computing devices, which may be located centrally or at distributed locations, that provide cloud-based services to various types of users and devices connected via a network such as the Internet via communications network 414. These cloud resources may include one or more content sources 416 and one or more media guidance data sources 418. In addition or in the alternative, the remote computing sites may include other user equipment devices, such as user television equipment 402, user computer equipment 404, and wireless user communications device 406. For example, the other user equipment devices may provide access to a stored copy of a video or a streamed video. In such embodiments, user equipment devices may operate in a peer-to-peer manner without communicating with a central server.

The cloud provides access to services, such as content storage, content sharing, or social networking services, among other examples, as well as access to any content described above, for user equipment devices. Services can be provided in the cloud through cloud computing service providers, or through other providers of online services. For example, the cloud-based services can include a content storage service, a content sharing site, a social networking site, or other services via which user-sourced content is distributed for viewing by others on connected devices. These cloud-based services may allow a user equipment device to store content to the cloud and to receive content from the cloud rather than storing content locally and accessing locally-stored content.

A user may use various content capture devices, such as camcorders, digital cameras with video mode, audio recorders, mobile phones, and handheld computing devices, to record content. The user can upload content to a content storage service on the cloud either directly, for example, from user computer equipment 404 or wireless user communications device 406 having content capture feature. Alternatively, the user can first transfer the content to a user equipment device, such as user computer equipment 404. The user equipment device storing the content uploads the content to the cloud using a data transmission service on communications network 414. In some embodiments, the user equipment device itself is a cloud resource, and other user equipment devices can access the content directly from the user equipment device on which the user stored the content.

Cloud resources may be accessed by a user equipment device using, for example, a web browser, a media guidance application, a desktop application, a mobile application, and/or any combination of access applications of the same. The user equipment device may be a cloud client that relies on cloud computing for application delivery, or the user equipment device may have some functionality without access to cloud resources. For example, some applications running on the user equipment device may be cloud applications, i.e., applications delivered as a service over the Internet, while other applications may be stored and run on the user equipment device. In some embodiments, a user device may receive content from multiple cloud resources simultaneously. For example, a user device can stream audio from one cloud resource while downloading content from a second cloud resource. Or a user device can download content from multiple cloud resources for more efficient downloading. In some embodiments, user equipment devices can use cloud resources for processing operations such as the processing operations performed by processing circuitry described in relation to FIG. 3.

Figure 5:
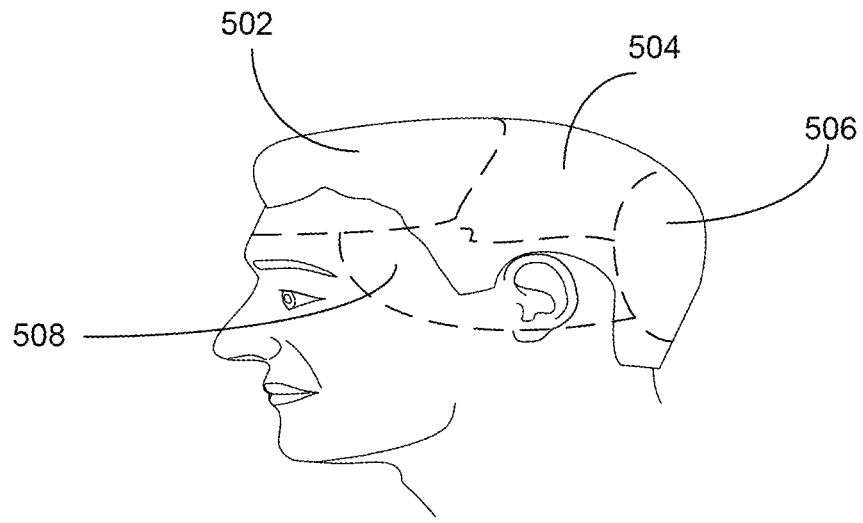
FIG. 5 shows a representation of a user and regions of the brain of the user associated with monitoring brain activity in accordance with some embodiments of the disclosure.
Figure 5:
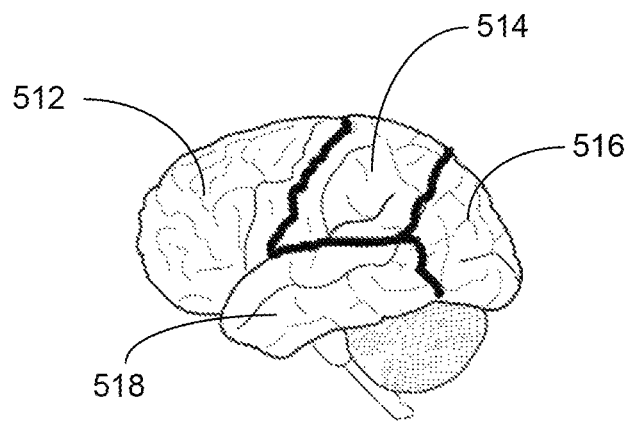

FIG. 5 shows a representation of a user and regions of the brain of the user associated with monitoring brain activity. For example, in some embodiments, the media guidance application may be implemented upon (or be in communication with) a user device that monitors brain activity of a user (e.g., via monitoring component 316 (FIG. 3)). The user device may reside upon the head of a user and include components (or sub-components) for testing different areas of the scalp of a user, or regions of the surface of a user's cranium.

For example, the scalp or cranium surface of user 500 includes first portion 502, second portion 504, third portion 506, and fourth portion 508. In some embodiments, each of first portion 502, second portion 504, third portion 506, and fourth portion 508 may correspond to a different region of brain 510. For example, in some embodiments, first portion 502 may correspond to frontal lobe 512, second portion 504 may correspond to parietal lobe 514, third portion 506 may correspond to occipital lobe 516, and fourth portion 508 may correspond to temporal lobe 518. Furthermore, any other aforementioned portions and/or regions may be associated with one or more positions and/or configurations of a user devices that is used to control a set of media guidance application operations.

For example, in some embodiments, the media guidance application may perform a media guidance application operation in response to brain activity detected in a particular region of the brain of a user. For example, the media guidance application may monitor brain activity of the user in portion 502 (e.g., using monitoring component 316 (FIG. 3)) and determine a first brain state associated with frontal lobe 512 of the monitored brain activity. The media guidance application may then cross-reference portion 502 with a database associated with functions performed by the user using regions of the brain to determine at least one function the user is performing based on the brain activity of the user in portion 502. For example, the cross-reference may reveal that frontal lobe 512 is associated with generating emotions and emotional responses in a user.

The media guidance application may then compare the first brain state to a threshold range for performing the at least one function, and in response to determining the first brain state does not correspond to the threshold range, performing a media guidance operation associated with the at least one function.

For example, the media guidance application may detect a state of the brain activity associated with frontal lobe 512 of the user. In response to determining that frontal lobe 512 is associated with emotions, the media guidance application of may compare the current brain state of the user to typical brain states (e.g., of the user or all users) associated with a particularly preferred emotion (e.g., happiness). In response to determining that the brain state of the user does not correspond to the preferred emotion (currently happy), the media guidance application may replace the media assets currently being consumed by or recommended to the user with a media asset with a higher likelihood of making the user happy.

In another example, the media guidance application may detect a state of the brain activity associated with various regions of the brain in order to perform a function. For example, the media guidance application may detect a state of the brain activity associated with occipital lobe 516 (e.g., associated with vision) and parietal lobe 514 (e.g., associated with reading) of the user. In response to determining that the brain state of the brain activity associated with occipital lobe 516 (e.g., associated with vision) and parietal lobe 514 (e.g., associated with reading) of the user does not correspond to the typical brain state of a user, while temporal lobe 518 (e.g., associated with hearing) does correspond to the typical brain state of the user, the media guidance application may modify the media assets, display settings, etc. such that text or important events are communicated to the user via verbal means (e.g., audio announcements).

Figure 6:
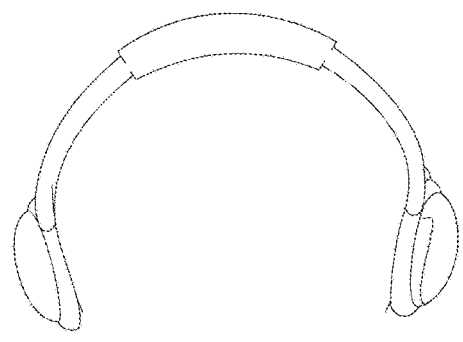
FIG. 6 shows multiple user devices that may be associated with monitoring brain activity in accordance with some embodiments of the disclosure.
Figure 6:
Figure 6:
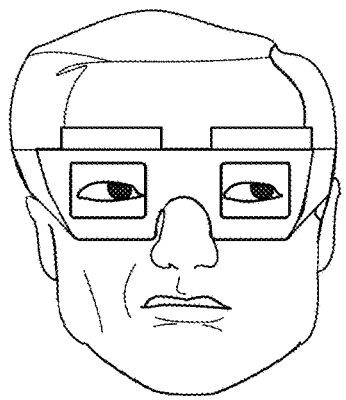
Figure 6:
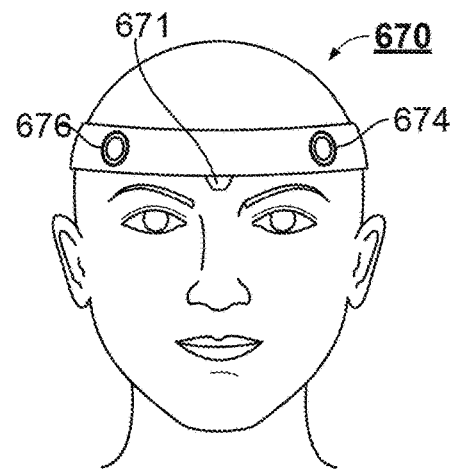
Figure 6:
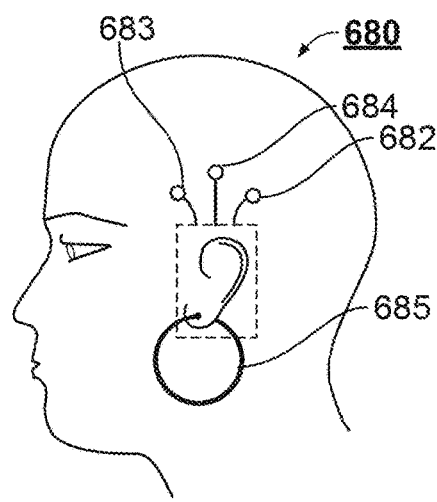
Figure 6:
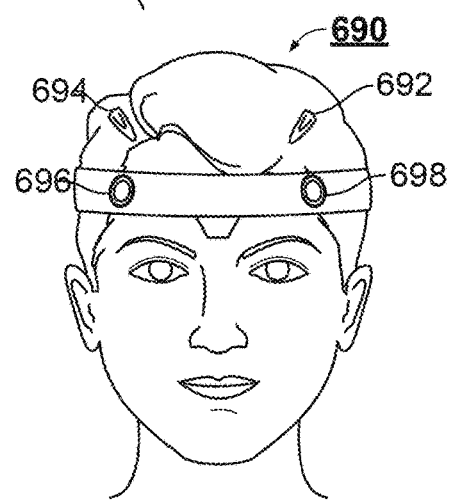

FIG. 6 shows multiple user devices that may be associated with monitoring brain activity. For example, a user device (e.g., upon which a media guidance application is implemented and/or which a media guidance application is in communication with) may be fashioned as a form of headwear.

For example, user device 600 is fashioned as a headset, user device 630 is fashioned as a hat/helmet, user device 660 is fashioned as eye glasses, user device 670 is fashioned as a headband, user device 680 is fashioned as jewelry, and user device 692 is fashioned as hair accessories. It should be noted that a user device configured to monitor brain activity as described herein may be fashioned as any headwear. Furthermore, in some embodiments, a user device may not be fashioned as headwear, but instead may be configured as any device capable of monitoring brain activity of a user, such as a wearable accessory. For example, any device which may incorporate and/or have access to an EEG, EMG, and/or other means for monitoring brain activity described herein may constitute a user device.

In some embodiments, the brain monitoring user devices may be categorized according to the number of parts. For example, the user devices may be classified into single part (such as headsets, headphones, etc), or may be categorized as multi-part (e.g., hair clips, earrings, other user devices or any combinations thereof).

In some embodiments the user device may include wearable accessories (e.g., jewelry such as a headlace, earring, adhesive pendant, or hair clip). For example, the wearable accessories may be a subset of headsets (e.g., headbands, etc.). For example, the headsets may be a subset of wearable accessories (e.g., wearable accessories may include a category of headsets such as headphones, or may include a category of jewelry such as earrings and pendants).

In some embodiments, a user device configured to monitor brain activity may be configured in categories based on function. For example, the user device may be ornamental (e.g., jewelry, earring, pendant, headlace, necklace, etc.), used as an article of clothing (e.g., a hat, a visor, a scarf, etc.), or used to enhance the senses of the user (e.g., eyeglasses, goggles, a monacle, a hearing aid, headphones, a nose clip, etc.).

In some embodiments, user devices 600, 630, 660, 670, 680 and 690 may further include additional sub-components (e.g., sub-components of monitoring component 316 (FIG. 3)), which may monitor brain activity on one or more regions of the brain. Sub-components may include electrodes or other features that may attach to the various portions (e.g., portions 502, 504, 506, and 508 (FIG. 5)) of a user (e.g., user 500 (FIG. 5)). Furthermore, in some embodiments, sub-components may extend and/or retract during various modes of the user device in order to accommodate the comfort of the user.

In some embodiments, user devices 600, 630, 660, 670, 680 and 690 may be battery-powered in order to provide a user with additional mobility. Furthermore, user devices 600, 630, 660, 670, 680 and 690 may include multiple modes, each corresponding to different power consumption levels and/or sensitivity levels.

In some embodiments, user device 670 may be shaped as a substantially circular fixture, such as a headband, headlace, a hat, or any other suitable substantially circular fixture. User device 670 may include sub-components 674 and 676 shaped as a pendant or accessory. Each of sub-components 674 and 676 may be a sub-component of monitoring component 316, such as a brain activity detector. User device 670 may include a component 671 which can be used to align user device 670 to a position on a user's cranium, for example by providing a reference point for the nasion of the user's cranium. Component 671 may be a sub-component of monitoring component 316 and may include a brain activity detector.

In some embodiments, user device 680 may be shaped as any type of jewelry, such as an earring, headlace, adhesive pendant, or any other suitable jewelry. User device 680 may include multiple subcomponents, shaped as parts of the jewelry. For example, user device 680 may include monitoring components 316, such as brain activity detectors 682, 683, and 684, shaped as jewels. Brain activity detectors 682, 683, and 684 may be electrodes that attach to specific detection locations on the cranium of a user. User device 680 may include an antenna or electrode 685, shaped as part of jewelry. For example, as an electrode, electrode 685 may act as a ground reference for EEG/EMG or any other suitable measurement of brain activity. For example, as an antenna, antenna 685 may communicate information wirelessly to other portions of user equipment.

In some embodiments, user device 690 may be shaped as accessories 692 and 694, such as hair clips. Accessories 692 and 694 may include sub-components of monitoring component 316 for monitoring brain signals.

In some embodiments, a brain monitoring user device does not need to contact the surface of a user's cranium. For example, a brain monitoring device may be an earring that includes a brain activity detector. Brain activity detectors are described further below in reference to FIG. 9. A brain activity detector may be able to detect or measure a brain signal without contacting the surface of the cranium. For example, the brain activity detector may include an IR thermal sensor that detects a brain temperature signal at a position on the user's cranium (e.g., illustrated in FIGS. 7-8). The brain temperature signal may correspond to brain activity at a brain portion corresponding to the position on the user's cranium.

For example, the brain activity detector may include a pulse oximeter that detects blood flow and oxygen content at a position on the user's cranium. The pulse oximeter may measure a brain blood flow or brain oxygen signal at a position of the user's cranium that corresponds to brain activity at a portion of the user's brain corresponding to the position on the user's cranium.

In some embodiments, any of user devices 600, 630, 660, 670, 680 and 690 may be used in any combination thereof. For example, user device 690, including accessories 692 and 694, may be used in conjunction with user device 695, including sub-components 696 and 698, which are substantially similar to user device 670 and sub-components 696 and 698. It should be understood that the above user devices are meant to be illustrative only, and any number of sub-components may be used.

Figure 7:
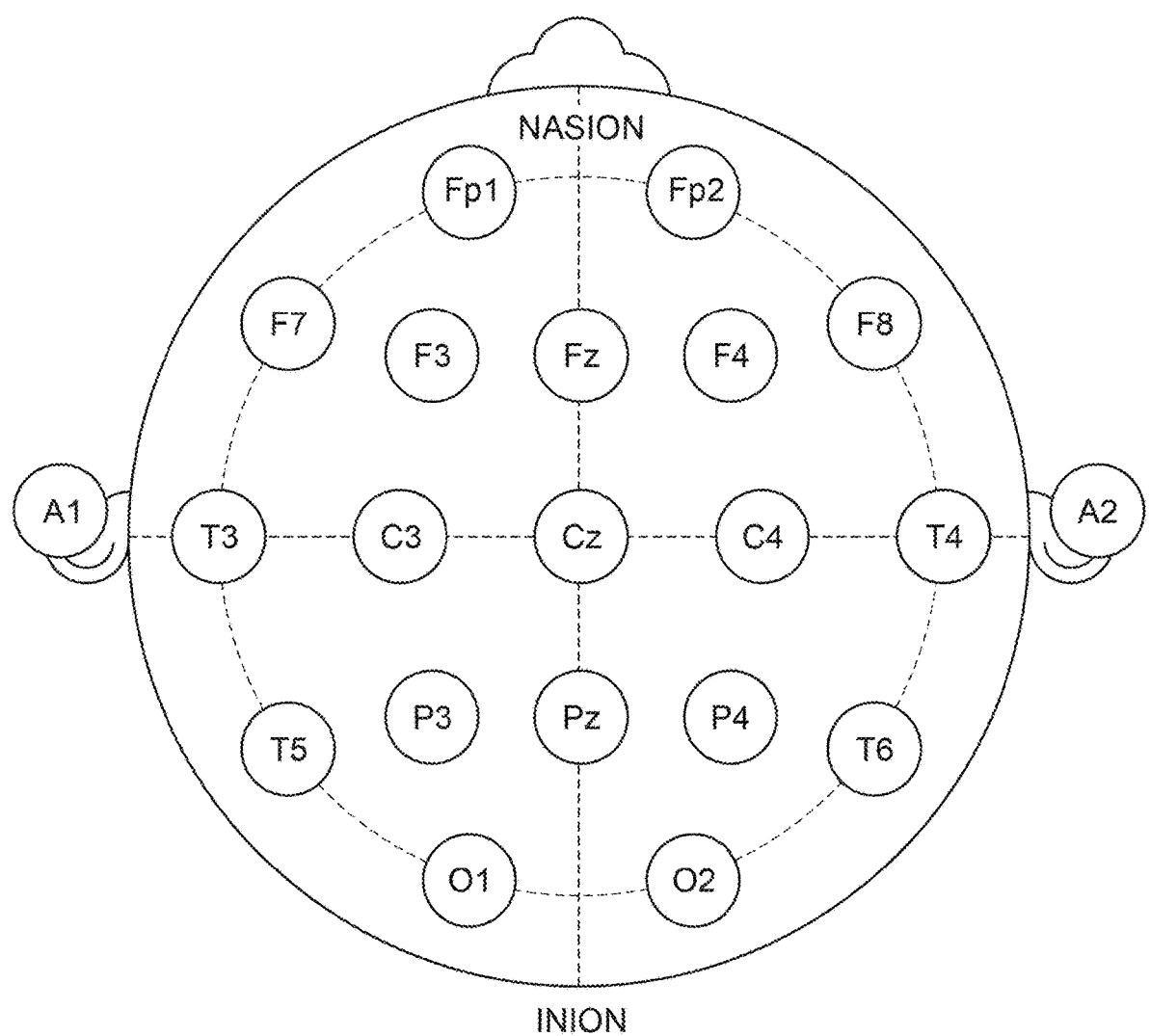
FIG. 7 is a top down diagram illustrating positions on a cranium where brain activity detectors may be placed to monitor brain activity of a user in accordance with some embodiments of the disclosure.

FIG. 7 is a top-down diagram illustrating positions on a cranium where brain activity detectors may be placed to monitor brain activity of a user. The positions illustrated correspond to a subset of the 10-20 system. Each position is labeled by at least a letter and a numeric index. The letter corresponds to a portion of a user's scalp and associated portion or region of a user's brain. For example, 'F' corresponds to the frontal lobe, 'P' corresponds to the parietal lobe, 'T' corresponds to the temporal lobe and 'O' corresponds to the occipital lobe. 'C' is used for identification purposes. The letter 'z' indicates that a brain activity detector is positioned on the midline. In addition to the letter codes "F, P, O and C", the letter code 'A' corresponds to the ear lobes, "Pg" corresponds to the nasopharyngeal lobe and "Fp" corresponds to the frontal polar position.

Each of the positions identified in FIG. 7 can detect brain activity from an associated lobe, brain portion or brain region. For example, position F7 may detect brain signals from the frontal lobe while position O14 may detect brain signals from the occipital lobe. Accordingly, if triggering a particular media guidance application operation is based on detecting brain signals associated with the frontal lobe, the media guidance application may require the user device (or a brain activity detector) to be at or near position F7.

Figure 8:
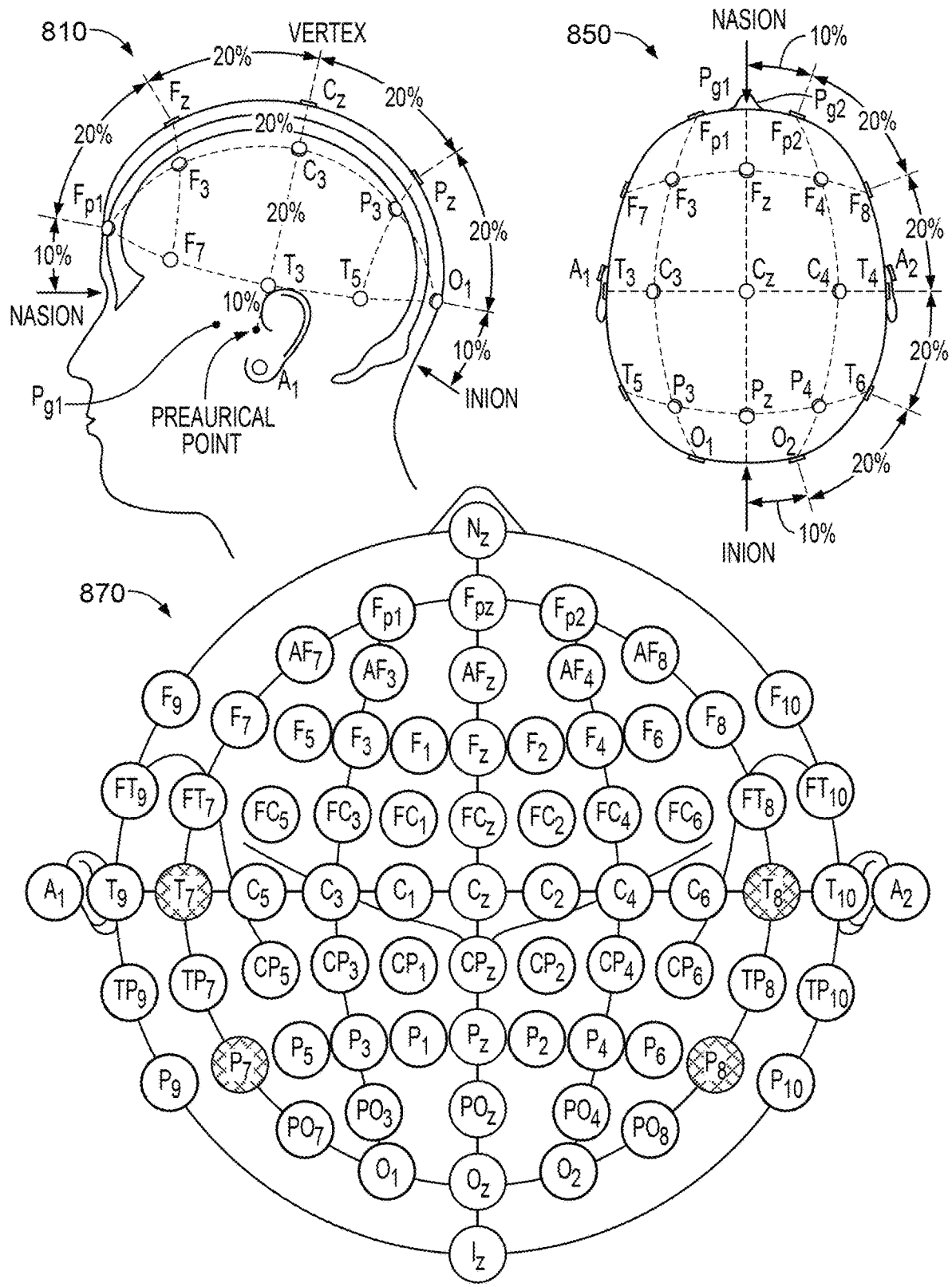
FIG. 8 shows detailed diagrams illustrating positions on a cranium where brain activity detectors may be placed to monitor brain activity of a user in accordance with some embodiments of the disclosure.

FIG. 8 shows detailed diagrams illustrating positions on a cranium where brain activity detectors may be placed to monitor brain activity of a user. Diagram 810 illustrates a side view of a user's cranium and corresponding positions for placement of brain activity detectors. Diagram 850 illustrates a top view of a user's cranium and corresponding positions for placement of brain activity detectors. Diagram 870 illustrates and labels "10%" positions as standardized by the American Electroencephalographic Society. The "10%" positions correspond to spacings of 10% of the total distance across an arc that traverses the outer surface of the cranium. These standardized positions provide common reference points for detecting information for corresponding brain regions. For example, position T3 corresponds to the temporal lobe located above the ear, and may correspond to hearing functions. Brain activity detectors positioned at T3 would measure brain signals indicative of hearing activity. For example, a media guidance application may determine that a user device is positioned at position O1 and provide media guidance application operations corresponding to eye blink patterns, such as a selection of channels or changing of channels.

The positions labeled and identified in FIG. 7 and FIG. 8 may correspond to positions for placement of brain activity detectors, and accordingly, placement of any of user devices 600, 630, 660, 670, 680 and 690, shown in FIG. 6. The position of a user device may be determined based on positions of sub-components of a user device relative to the positions labeled and identified in FIG. 7 and FIG. 8.

Figure 9:
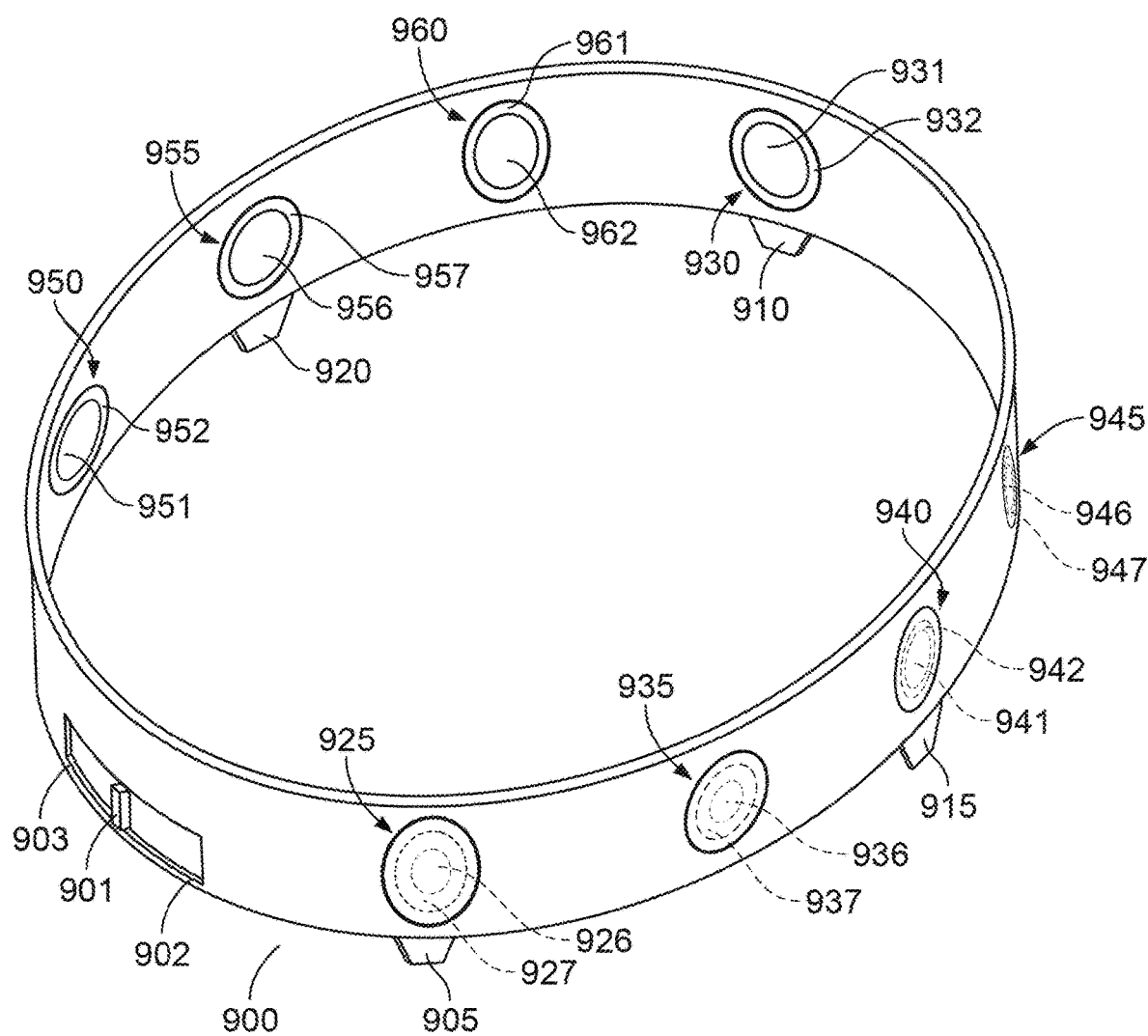
FIG. 9 shows a substantially circular user device that may be used to monitor brain activity in accordance with some embodiments of the disclosure.

FIG. 9 shows a user device 900, as a substantially circular fixture, which may be used to monitor brain activity. The substantially circular user device may correspond to user device 670. In some embodiments, user device 900 may include alignment fixtures 905, 910, 916 and 920. These fixtures may be used to position user device 900 on a cranium of a user. For example, fixture 905 may be positioned on the nasion, fixture 910 may be positioned on the ision, fixture 920 may be positioned on the right ear, and fixture 915 may be positioned on the left ear.

In some embodiments, user device 900 may include a switch 901, which may be moved between positions 902 and 903, or any position between positions 902 and 903. Each of these positions may represent a configuration of user device 900. The position of switch 901 may affect media guidance application operations that may be provided by a media guidance application.

In some embodiments, user device 900 may include one or more sub-components 925, 930, 935, 940, 945, 950, 955, and 960. Each of said sub-components may be used as a brain activity detector. Each of said sub-components may be a sub-component of monitoring equipment 316.

In some embodiments, each of said sub-components may include one or more parts that are used to detect brain signals. For example, sub-component 925 may include a brain activity detector 926 and an additional detector 927. Brain activity detector 926 may be an electrode or sensor for measuring EEG signals, EMG signals or any other suitable signals. The quality of an EEG signal may depend on a quality of electrical contact between a sensor and a skin surface of a cranium. To assist in the calibration of an EEG measurement, additional sensor 927 may be used.

In some embodiments, additional detector 927 may be located around or proximate to brain activity detector 926. Additional detector 927 may measure any type of metric that facilitates determination of a quality of a detected brain signal. The metric may be any suitable measurement that corresponds to the type of detector. For example, if the detector is a temperature detector, the metric may be temperature. For example, additional detector 927 may be an optical source and optical sensor that measures the absorbance by blood vessels, such as a pulse oximeter. By measuring, using the optical sensor, the reflectance of light emitted by the optical source, it may be possible to determine whether there any obstructions between sub-component 925 and the skin surface of a cranium. For example, the metric of this additional detector that includes an optical source and optical detector may be an oxygen concentration, or distance of the detector from the surface of the skin. Based on this information, the brain signal detected by brain activity detector 926 may be scaled accordingly. For example, in response to determining that the brain activity detector is a distance from the scalp, the media guidance application may scale the intensity of brain signals (e.g., those illustrate in FIG. 11) by a percentage corresponding to the distance from the scalp.

In some embodiments, control circuitry 304 of user device 900 may generate a message for display to a user instructing the user to reposition the brain monitoring user device to improve contact (e.g., electrical contact) between the brain activity detectors and the skin surface of the user's cranium.

In some embodiments, additional detector 927 may be a temperature sensor. Based on the temperature detected, it may be possible to determine whether there is sufficient contact with a skin surface of a cranium. Based on the sensed temperature, the brain signal detected by the brain activity detector may be scaled accordingly. For example, the media guidance application may scale a brain signal measured by a brain activity detector if it determines that the brain activity detector is not in contact with the skin. For example, the media guidance application may determine that the measured temperature is below an expected scalp temperature. The media guidance application may determine a scaling factor based on the difference between the measured temperature and the expected temperature and scale the measured brain signal.

In some embodiments, the media guidance application may determine whether the signal strength of the brain signal detected by brain activity detector 926 is of sufficient strength for use in determining a brain state of a user. For example, the media guidance application may determine whether the brain signal detected by brain activity detector 926 is above a signal to noise ratio (SNR).

In some embodiments, non-contact brain activity detectors and additional detectors may be used to measure and determine brain signals. For example, IR sensors may be used to measure temperature, optical sources and optical sensors may be used to determine blood flow. Based on these non-contact measurements, a brain signal may be detected.

In some embodiments, each of sub-components 930, 935, 940, 945, 950, 955, and 960 may be substantially similar to sub-component 925. For example, each of brain activity detectors 931, 936, 941, 946, 951, 956 and 961 and additional detectors 932, 937, 942, 947, 952, 957 and 962 may be substantially similar to brain activity detector 926 and additional detector 927, respectively. Each of the sub-components may be shaped as jewelry, pendants or any other suitable shape. Although user device 900 is illustrated with six sub-components 930, 935, 940, 945, 950, 955, and 960 disposed at equal spacing around user device 900, it should be understood that any number of sub-components may be used and disposed at any distance around user device 900.

Figure 10:
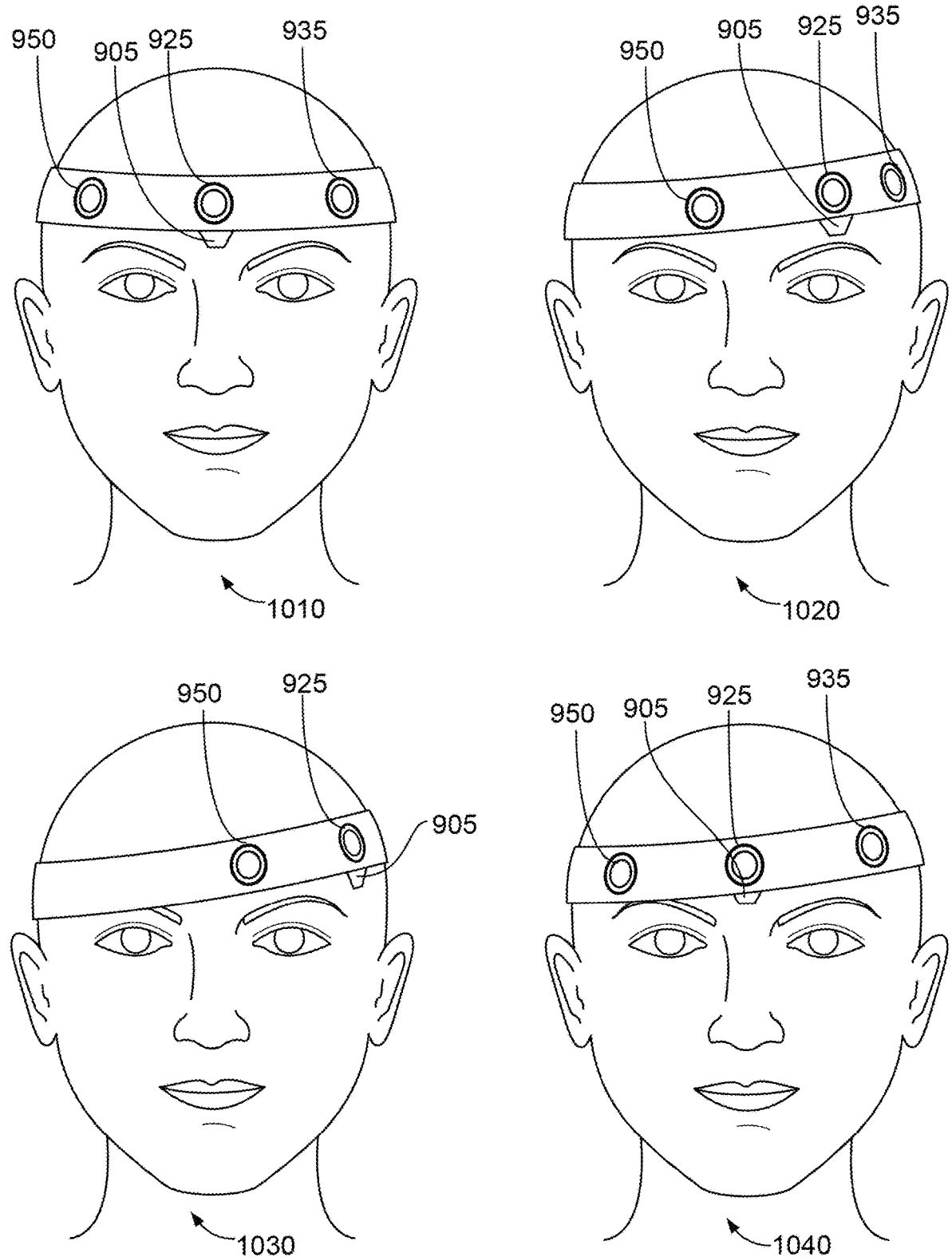
FIG. 10 illustrates configurations of a user device that may affect operations provided by an application in accordance with some embodiments of the disclosure.

FIG. 10 illustrates configurations of a user device that may affect operations provided by an application. The configuration of a user device may affect the brain signals that a brain activity detector may measure at a particular position. Positions on the cranium will be described in reference to the positions illustrated in FIG. 7 and FIG. 8. The configurations illustrated by FIG. 10 are relative to user device 900. The configurations in FIG. 10 may be the result of moving user device 900 by rotation about the cranium, tilt about the cranium, translation about the cranium, or any combination thereof. Furthermore, it should be noted that user device 900 may be incorporated into jewelry, a headband, eye-glasses, hat, etc. in order to be aesthetically pleasing.

For example, configuration 1010 illustrates user device 900 positioned on a cranium of a user such that sub-component 925 is located at the nasion, over position FPz, sub-component 935 is located at position F7, and sub-component 950 is located at position F8. For example, in configuration 1010, the brain signals may be measured from a first part of the frontal lobe. A media guidance application may determine that the first part of the frontal lobe corresponds to happy emotional brain states, and determine whether the user is in a particular emotional brain state, and provide media guidance application operations such as recommendations of media assets based on the emotional state of the user.

For example, configuration 1020 illustrates user device 900 in a position that is rotated about the cranium relative to configuration 1010. In configuration 1020, sub-component 925 is located at position Fp1, sub-component 935 is located at position F7, and sub-component 950 is located over position Fp2. For example, in configuration 1020, the brain signals may be measured from a second part of the frontal lobe. A media guidance application may determine that the second part of the frontal lobe corresponds to an attention level of a user, and provide media guidance application operations based on the attention level of the user.

For example, configuration 1030 illustrates user device 900 in a position that is further rotated about the cranium relative to configuration 1020. In configuration 1030, sub-component 925 is located at position T3, sub-component 935 is located at position O1 (not shown), and sub-component 950 is located over position Fp1. For example, in configuration 1030, the brain signals may be measured from the frontal lobe, temporal lobe, and occipital lobe. A media guidance application may determine that brain signals are detectable from the frontal lobe, the temporal lobe, and the occipital lobe. For example, the media guidance application may cross-reference measured brain signals with a brain signals/locations database to determine locations of brain activity detectors used to measure the brain signals. The media guidance application may then cross-reference the positions of the brain activity detectors with a cranium location/brain portion database to determine brain portions corresponding to the positions of each of the brain activity detectors. The media guidance application may then cross-reference the brain portions with a brain portion/operations database to determine a set of media guidance application operations to provide to the user.

For example, the media guidance application may determine eye blink brain states from brain signals measured from the occipital lobe and that mood brain states can be determined from measurements of brain signals from the frontal lobe. The media guidance application may provide channel changing operations that are controlled by eye blink brain states, and may provide recommendation operations that are affected by mood brain states based on the cross-reference with the brain portions/operations database. In such cases, depending on what media guidance application operation the user wishes to control, the user may change the configuration and/or position of the user device such that the brain state needed to trigger the desired media guidance application operation may be monitored by the user device.

For example, configuration 1040 illustrates user device 900 in a position that is tilted about the cranium relative to configuration 1010. In configuration 1030, sub-component 925 is located at position Fpz, sub-component 935 is located at position F3, and sub-component 950 is located below position F8. For example, in configuration 1040, the brain signals may be measured from a third part of the frontal lobe. A media guidance application may determine that the third part of the frontal lobe corresponds to a particular level of alpha waves (e.g., as discussed below in relation to FIG. 11). Accordingly, if a user wishes to access media guidance application operations triggered by a particular level of alpha waves (and/or a deviation therefrom), the media guidance application may prompt the user to re-configure or re-position the user device into configuration 1040.

In each of the above described configurations, sub-components 925, 935 and 950 are located over different positions of the cranium corresponding to different brain portions. The location of each sub-component in user device 900, or a sub-component of monitoring equipment 316, affects the type of brain signal that can be detected by the sub-component. For example, configuration 1030 can measure from position O1 corresponding to the occipital lobe, which configuration 1010 does not. It should be understood that the positions of the user devices in FIG. 10 are not drawn to scale.

Figure 11:
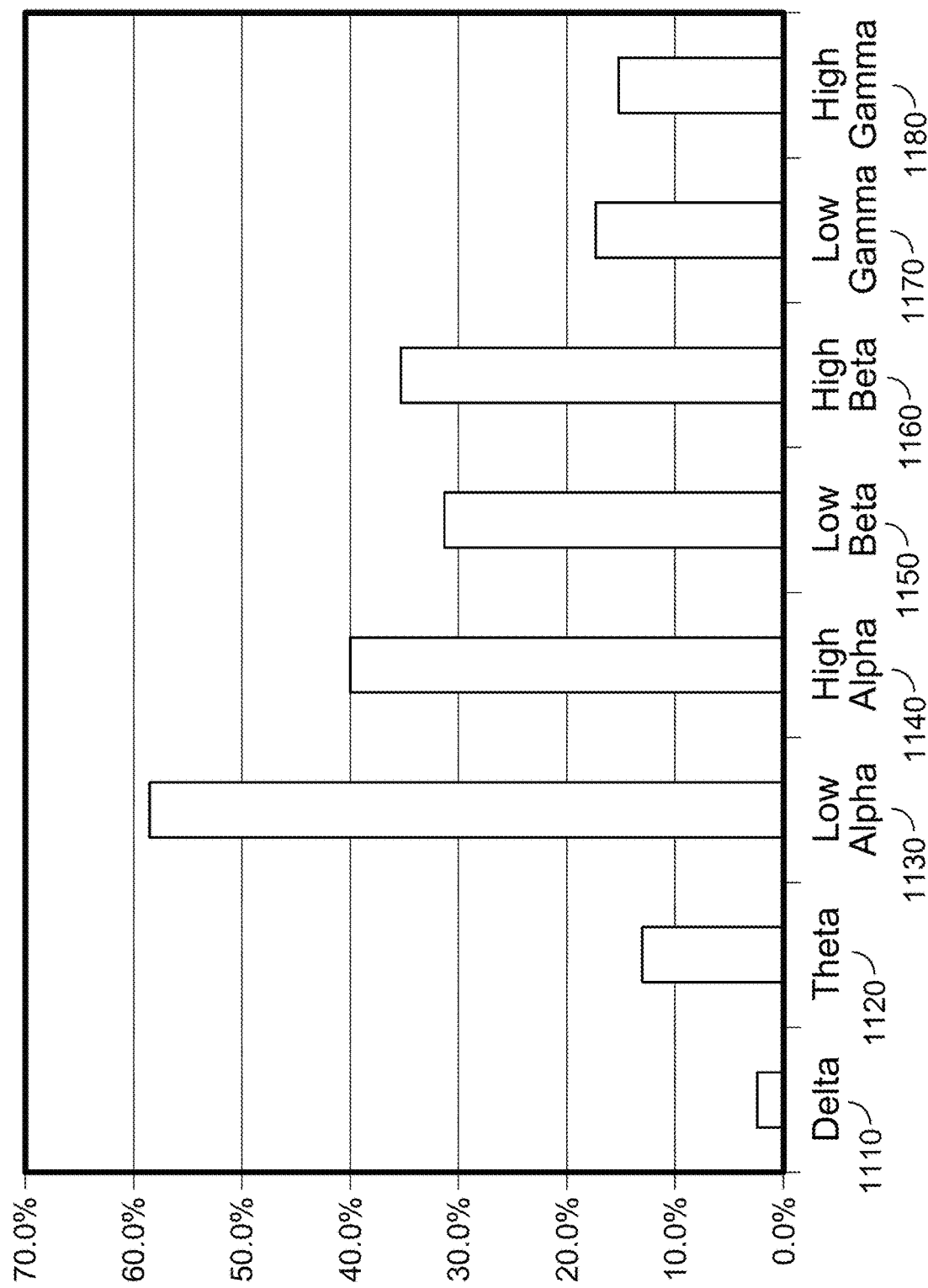
FIG. 11 illustrates a brain wave signal in accordance with some embodiments of the disclosure.

FIG. 11 illustrates an example of a brain wave signal. In some embodiments, a brain wave signal may be an EEG signal. As described above, an EEG signal may have a plurality of constituent signals, each corresponding to a different frequency band. As referred to herein, a "constituent signal" may refer to a portion of a signal that may be distinguished by frequency band, intensity range, coefficients of a mathematical transform of the signal such as a fourier transform, or any other suitable portion. As referred to herein, a sub-band signal may be any portion of a constituent signal that may be distinguished by frequency band, intensity range, coefficients of a mathematical transform of the constituent signal such as a fourier transform, or any other suitable portion. Each of the constituent signals may include one or more sub-band signals. The brain wave signal illustrated in FIG. 11 includes a delta band constituent signal 1110, a theta band constituent signal 1120, a low alpha band sub-band signal 1130, high alpha band sub-band signal 1140, low beta band sub-band signal 1150, high beta band sub-band signal 1160, low gamma band sub-band signal, and a high gamma band sub-band signal. Although two constituent signals and 6 sub-band signals are illustrated in FIG. 11, it should be understood that a brain wave signal may include any number of suitable constituent signals. The x-axis of FIG. 11 illustrates the constituent signals labeled by frequency band. The y-axis of FIG. 11 illustrates a scaled intensity of each constituent signal. The constituent signals of FIG. 11 may be determined from a measured EEG by performing a transform on the EEG, such as a Fourier transform, LaPlace transform, Z-Transform, or any other suitable transform.

The characteristics of a set of constituent signals within a brain wave signal may be used to identify one of the locations on the cranium as illustrated in FIG. 7 and FIG. 8. These characteristics may be static (constant across measurement time) or dynamic (varying across measurement time). The characteristics may be, for example, a metric of the relative intensities. For example, a first brain wave signal corresponding to a first location within a brain region (e.g., the frontal lobe) may have a different set of characteristics than a second brain wave signal corresponding to a second location within the same brain region. For example, a brain wave signal measured at position Fp1 may have different characteristics than a brain wave signal measured at position F3.

For example, a first brain wave signal corresponding to location for a first brain region (e.g., the temporal lobe) may have characteristics that are different than a second brain wave signal corresponding to a second location within a second brain region (e.g., the occipital lobe). For example, a brain wave signal measured at position T3 may have different characteristics than a brain wave signal measured at position O2. Based on these brain wave signals, the media guidance application may determine a position of a brain activity detector by cross-referencing a measured brain signal with a brain-signal-positions database as described above, to determine at which of the locations illustrated in FIGS. 7 and 8, a brain activity detector is positioned.

Figure 12:
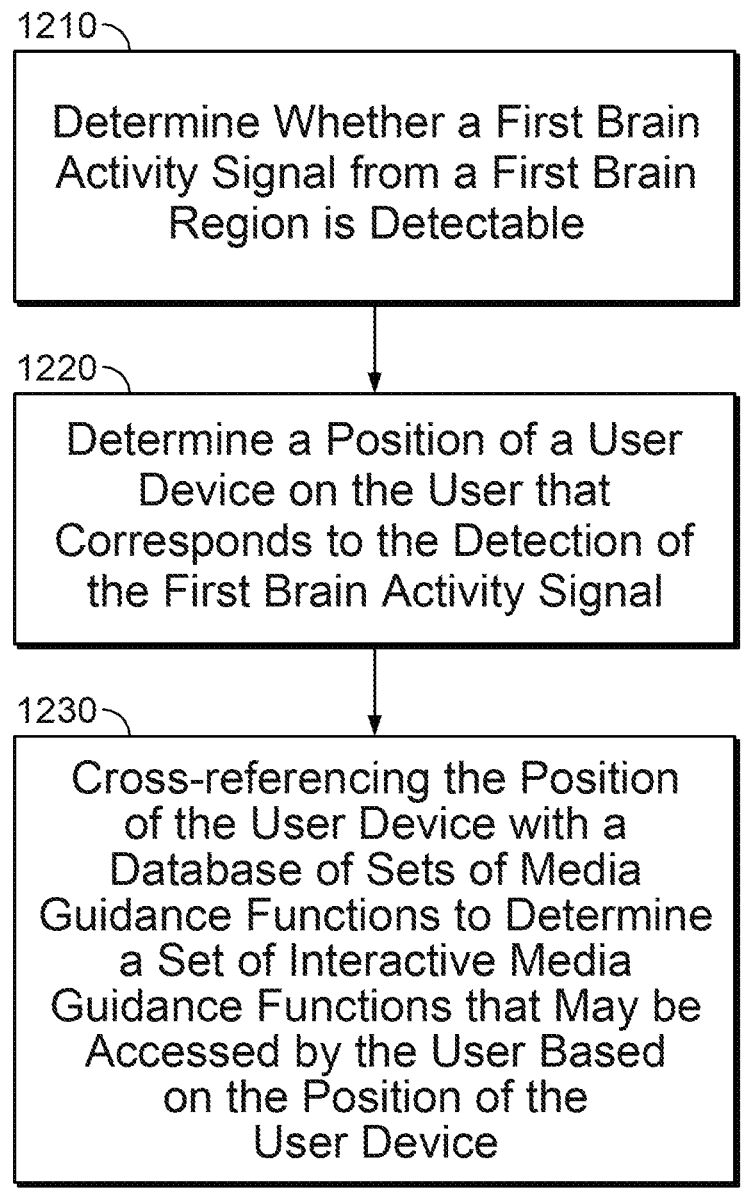
FIG. 12 is a flow chart of illustrative steps involved in determining a configuration of a brain monitoring user device, and providing operations of an application in accordance with some embodiments of the disclosure.

FIG. 12 is a flow chart of illustrative steps involved in determining a configuration of a brain monitoring user device. It should be noted that process 1200, or any step thereof, could be performed in any suitable order and provided by any of the devices shown in FIGS. 3-4 and 6. For example, process 1200 may be executed by control circuitry 304 (FIG. 3) on user equipment device 402, 404 and/or 406 (FIG. 4) any of which may be configured as any of the user devices shown in FIG. 6, as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 700 may be incorporated into or combined with one or more steps of any other process (e.g., as described in FIG. 13).

At step 1210, the media guidance application determines whether a first brain signal from a first brain region is detectable. For example, the media guidance application (e.g., implemented on user device 300 (FIG. 3)) may receive data (e.g., from monitoring component 316 (FIG. 3)) associated with the brain activity (e.g., the current frequency range of voltage fluctuations in the brain and/or electrical activity of muscles of the brain at rest and during contraction) of a user (e.g., user 500 (FIG. 5)). The media guidance application may poll each of the sub-components 925, 930, 935, 940, 945, 950, 955 and 960 to determine if the detected brain wave signal corresponds to a threshold. As referred to here, a "threshold" may refer to a frequency or intensity of a brain signal that defines a level at which the brain signal is detectable.

In some embodiments, the media guidance application may continuously monitor the brain activity of a user using an EEG, EMG, or suitable device for monitoring brain waves (e.g., incorporated as a sub-component of monitoring component 316 (FIG. 3)). Alternatively, the media guidance application may periodically poll the brain activity of a user (e.g., on a predetermined schedule and/or in response to a user input, (i.e., selecting selectable option 204 (FIG. 2)).

In some embodiments, the media guidance application may trigger (e.g., via control circuitry 304 (FIG. 3)) various modes for monitoring brain activity, in which each mode is associated with a different power consumption level and/or sensitivity level. For example, the media guidance application (e.g., via control circuitry 304 (FIG. 3)) may induce different modes of a monitoring component (e.g., monitoring component 316 (FIG. 3)) in response to instructions and/or information received from a power management unit (e.g., PMU 318 (FIG. 3)) in order to extend the life of an energy storage device or limit the exposure of a user (e.g., user 500 (FIG. 5)) to activities of the monitoring component.

At step 1220, the media guidance application determines a position of a user device on the user that corresponds to the detection of the first brain signal. For example, the media guidance application (e.g., implemented on user device 300 (FIG. 3)) may receive data (e.g., from a sub-component of monitoring component 316 (FIG. 3)) associated with the brain activity (e.g., the current frequency range of voltage fluctuations in the brain and/or electrical activity of muscles at rest and during contraction) of a position on the cranium (e.g., any of the positions in FIGS. 7-8) of a user (e.g., user 500 (FIG. 5)). The media guidance application may receive a first brain signal (e.g., of the form shown in FIG. 11) from sub-component 925 of user device 900. The received brain signal may be correlated by control circuitry 304 with a set of characteristic brain signals, each corresponding to a location on the cranium of a user. Control circuitry 304 may select the position on the cranium corresponding to the highest correlated characteristic brain signal. By selecting the position corresponding to the highest correlated characteristic brain signal, the control circuitry may have determined the position of sub-component 925 of user device 900 on the cranium of the user. Furthermore, by receiving multiple brain signals at multiple brain activity detectors, the media guidance application may detect the particular configuration of user device 900 (e.g., a hat worn frontwards or backwards).

For example, the media guidance application may cross-reference brain signals measured from each of a number of brain activity detectors on a user device with a brain signals-location database in order to determine positions of each of the brain activity detectors. The media guidance application may determine a position of the user device based on the positions of the brain activity detectors on a user's cranium and the positions of the brain activity detectors on the user device.

At step 1230, the media guidance application cross-references the position of the user device with a database of sets of media guidance application operations to determine a set of interactive media guidance application operations that may be accessed by the user based on the position of the user device. As described above in reference to FIG. 10 and FIG. 11, the position of user device 900 (or any other suitable user device illustrated in FIGS. 3, 4 and 6), may affect the brain portion from which brain activity can be measured.

Furthermore, each brain portion may be associated with different types of functioning and brain states (e.g., the frontal lobe is associated with mood brain states while the occipital lobe is associated with eye blink brain states). Based on the location of the user device, and brain portions from which brain activity can be measured, control circuitry 304 may select a set of operations that are provided by the media guidance application. For example, control circuitry 304 may, in response to determining the position of user device 900 and determining that the corresponding brain portion is the occipital lobe (associated with eye blink brain states), enable channel changing operations. For example, control circuitry 304 may, in response to determining the position of user device 900 and determining that the corresponding brain portion is the parietal lobe (associated with attention), enable volume changing operations.

The media guidance application may (e.g., via control circuitry 304 (FIG. 3)) cross-reference the determined positions of brain activity detectors of the user device with a database (e.g., stored locally on storage 308 (FIG. 3) or stored remotely at media guidance data source 418 (FIG. 4), and/or any location accessible via communications network 414 (FIG. 4)) associated with characteristic brain signals and corresponding positions of the cranium. For example, the database may include records correlating brain signals to each of a plurality of locations on the cranium, correlating each of the plurality of locations to brain portions, and correlating each of the brain portions to media guidance application operations.

Figure 13:
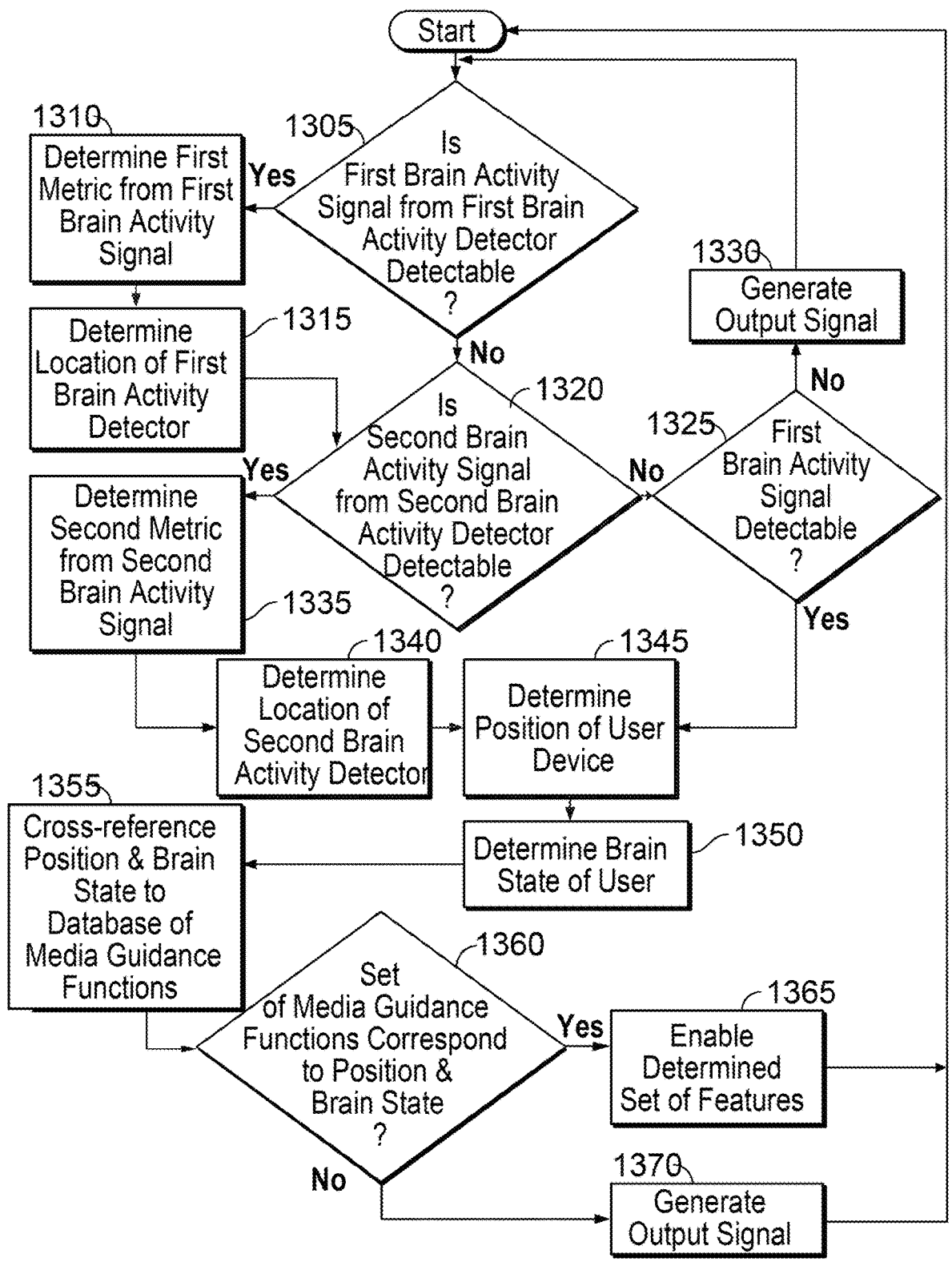
FIG. 13 is a flow chart of illustrative steps involved in determining a configuration of a brain monitoring user device based on brain signals detected from brain activity sensors, and providing operations of an application in accordance with some embodiments of the disclosure.

FIG. 13 is a flow chart of illustrative steps involved in determining a configuration of a brain monitoring user device based on brain signals detected from brain activity sensors. It should be noted that process 1300 or any step thereof could be displayed on, or provided by, any of the devices shown in FIGS. 3-4 and 6 in response to brain activity of a user (e.g., user 500 (FIG. 5)). For example, process 1300 may be executed by control circuitry 304 (FIG. 3) on user equipment device 402, 404, and/or 406 (FIG. 4) any of which may be configured as headwear (e.g., as shown in FIG. 6) as instructed by the media guidance application while a user is consuming media content (e.g., displayed on display 100 (FIG. 1A), display 130 (FIG. 1B), display 150 (FIG. 1C), and/or display 200 (FIG. 2)). In addition, one or more steps of process 800 may be incorporated into, or combined with, one or more steps of any other process (e.g., as described in FIG. 11).

At step 1305, the media guidance application determines whether a first brain signal from a first brain activity sensor (e.g., a sub-component of monitoring equipment 316 or any of sub-components 925, 930, 935, 940, 945, 950, 955, and 960) is detectable. For example, the media guidance application may receive a signal from a brain activity detector (e.g., any of brain activity detectors 926, 931, 936, 941, 946, 951, 956, and 961) and/or an additional detector (e.g., any of additional detectors 927, 932, 937, 942, 947, 952, 957, and 962). For example, control circuitry 304 may receive a signal and determine whether the signal corresponds to a threshold. In response to determining that the received signal corresponds to a threshold, control circuitry 304 may determine that the signal is detectable. In the alternative, in response to determining that the received signal does not correspond to the threshold, control circuitry 304 may determine that the signal is not detectable.

If the media guidance application (e.g., implemented on control circuitry 304) determines that the first brain signal is detectable, the control circuitry is directed by the media guidance application to proceed to step 1310. If the media guidance application determines that the first brain signal is not detectable, the control circuitry is directed by the media guidance application to proceed to step 1320.

At step 1310, the control circuitry 304 determines a first metric from the first brain signal. In some embodiments, the metric may be a scalar value. For example, control circuitry 304 may compute a weighted average of the intensities of components. In reference to FIG. 11, control circuitry 304 may compute a weighted average of all or a subset of constituent signals 1110, 1120, 1130, 1140, 1150, 1160, 1170, and 1180.

In some embodiments, the metric may be a vector. For example, in reference a subset of the constituent signals may be extracted and transformed into a feature vector for subsequent comparison.

At step 1315, the media guidance application determines a position of the first brain activity sensor. In some embodiments, control circuitry 304 may cross-reference the metric determined in step 1310 with a database that stores records correlating metrics with reference locations on a cranium (e.g., stored in storage 308) to determine a position of a brain activity detector (e.g., any of brain activity detectors 926, 931, 936, 941, 946, 951, 956, and 961) on a cranium of a user (e.g., any of the positions illustrated in FIG. 7 and FIG. 8). After determining the location of the first brain activity detector, control circuitry 304 proceeds to step 1320.

At step 1320, the media guidance application determines whether a second brain signal from a second brain activity detector (e.g., a sub-component of monitoring equipment 316 or any of sub-components 925, 930, 935, 940, 945, 950, 955, and 960) is detectable. For example, the media guidance application may receive a signal from a brain activity detector (e.g., any of brain activity detectors 926, 931, 936, 941, 946, 951, 956, and 961) and/or additional detector (e.g., any of additional detectors 927, 932, 937, 942, 947, 952, 957, and 962). For example, control circuitry 304 may receive a signal and determine whether the signal corresponds to a threshold. In response to determining that the received signal corresponds to a threshold, control circuitry 304 may determine that the signal is detectable. In the alternative, in response to determining that the received signal does not correspond to a threshold, control circuitry 304 may determine that the signal is not detectable.

If the media guidance application determines that the second brain signal is detectable, the control circuitry 304 is directed by the media guidance application to proceed to step 1335. If the control circuitry 304 determines that the first brain signal is not detectable, the control circuitry is directed by the media guidance application to proceed to step 1325.

At step 1325, the media guidance application determines whether the first brain signal from the first brain activity sensor was detectable. In some embodiments, the control circuitry may have previously stored (e.g., in storage 308) whether the first brain signal was detectable at step 1305. In performing step 1325, the control circuitry may check the storage 308 to determine whether the first brain signal was detectable.

In some embodiments, the media guidance application may repeat the process described in step 1305 to determine whether the first brain signal is detectable, for example, if the position of the user device (e.g., a device of FIG. 3, user equipment device 404, wireless user communications device 406, or device of FIG. 6) has been changed between step 1305 and step 1325.

In response to determining that the first brain signal is not detectable, media guidance application instructs control circuitry 304 to proceed to step 1330. In response to determining that the first brain signal is detectable, control circuitry 304 proceeds to step 1345.

At step 1330, media guidance application has determined that neither the first brain signal nor second brain signal is detectable. In some embodiments, control circuitry generates an output signal. The information conveyed by the output signal may indicate an error condition. For example, control circuitry 304 may indicate that the onboard power management unit is faulty, or may indicate any other error with the user device that requires servicing.

In some embodiments, media guidance application may determine, based on information from the first and second brain activity detectors (e.g., any of brain activity detectors 926, 931, 936, 941, 946, 951, 956, and 961) and/or information from additional detectors (e.g., any of additional detectors 927, 932, 937, 942, 947, 952, 957, and 962), that there is poor contact between the brain activity detector and the scalp surface of the cranium. For example, if there is poor electrical contact, an EEG signal may not be measured with sufficient strength. In response to determining that the brain activity detector is not making contact with the skin surface, control circuitry 304 may generate an output signal for display (e.g., on display 312 of FIG. 3 or any of user television equipment 408, user computer equipment 404, or wireless communications device 406) that the user device must be adjusted. From step 1330, control circuitry restarts process 1300 by proceeding to step 1305.

At step 1335, media guidance application determines a second metric from the second brain signal. In some embodiments, the metric may be a scalar value. For example, control circuitry 304 may compute a weighted average of the intensities of components. In reference to FIG. 11, control circuitry 304 may compute a weighted average of all or a subset of constituent signals 1110, 1120, 1130, 1140, 1150, 1160, 1170, and 1180.

In some embodiments, the metric may be a vector. For example, in reference to FIG. 11 a subset of the constituent signals may be extracted and transformed into a feature vector for subsequent comparison.

At step 1340, media guidance application determines the location of the second brain activity detector. In some embodiments, control circuitry 304 may cross-reference the metric determined in step 1335 with a database that stores records correlating metrics with reference locations on a cranium (e.g., stored in storage 308) to determine a position of a brain activity detector (e.g., any of brain activity detectors 926, 931, 936, 941, 946, 951, 956, and 961) on a cranium of a user (e.g., any of the positions illustrated in FIG. 7 and FIG. 8). After determining the position of the second brain activity detector, control circuitry 304 proceeds to step 1345.

At step 1345, media guidance application determines a position or configuration of the user device. In some embodiments, the user device may be a plurality of separate parts (e.g., accessories 692 and 694). For example, each of accessories 692 and 694 may include first and second brain activity detectors, respectively. Control circuitry 304, having determined the positions on the cranium of each of the first and second brain activity detectors in steps 1315 and 1340 will have already determined the position of each accessory.

For example, as illustrated in FIG. 6, user device 690 may include accessories 694 and 692 (e.g., hair clips), which are positioned over F3 and F4, and user device 690 (e.g., a headband) which includes brain activity detectors 696 and 698 positioned over locations F7 and F8. Each of these locations may correspond to portions of the frontal lobe that measure a different emotional state. For example, F3 may correspond to a location that is indicative of anger, F4 may correspond to a location that is indicative of sadness, F7 may correspond to a location that is indicative of happiness, and F8 may correspond to a location that is indicative of boredom. Media guidance application may determine whether each of the brain signals measured by brain activity detectors at 692, 694, 696 and 698 are detectable by determining whether the brain signals correspond to a threshold. Media guidance application may then determine the positions of each of 692, 694, 696, and 698 by determining the positions of corresponding brain activity detectors.

The media guidance application may do this by cross-referencing the measured brain signals with a brain-signal-positions database. Media guidance application may then determine that the frontal lobe is monitored and provide a set of media guidance application operations based on mood brain states, which can be monitored by the frontal lobe. For example, the media guidance application may provide recommendations in response to determining that the frontal lobe, and therefore moods, can be monitored.

In some embodiments, the first and second brain activity detectors may be disposed on the same user device (e.g., user device 670, 680, etc.). In some embodiments, control circuitry 304 may have already determined the positions or at least estimates of the positions of each of the first and second brain activity detectors. Control circuitry 304 may refine the determined positions based on the structure of the user device and the known positions of the first and second brain activity detectors on the user device. Control circuitry 304 next proceeds to step 1350.

At step 1350, media guidance application determines a brain state of the user. For example, the media guidance application may receive data from a monitoring component (e.g., monitoring component 316 (FIG. 3)) incorporated into and/or in communication with (e.g., via communications network 414 (FIG. 4) a user device (e.g., user device 300 (FIG. 3) and/or user equipment device 402, 404, and/or 406 (FIG. 4), and/or any of user devices 600, 630, 660, 670, 680, and 690 (FIG. 6)) upon which the media guidance application is implemented. The media guidance application may (e.g., via control circuitry 304 (FIG. 3)) process that data to determine a brain state that corresponds with the retrieved data. For example, a metric of the received data may correspond to a particular frequency range and/or electrical activity of the muscles near a particular region or electrical activity in a particular region (e.g., frontal lobe 512 (FIG. 5)) of a brain (e.g., brain 510 (FIG. 5)) of the user.

The media guidance application may then cross-reference the frequency range of the brain activity of the user with a database stored locally on storage 308 (FIG. 3) or stored remotely at media guidance data source 418 (FIG. 4), and/or any location accessible via communications network 414 (FIG. 4)) associated with frequencies of brain states and corresponding moods to determine a current mood of the user and/or cross-reference the electrical activity of the muscles near the brain or electrical activity in the brain of the user with a database (e.g., stored locally on storage 308 (FIG. 3) or stored remotely at media guidance data source 418 (FIG. 4), and/or any location accessible via communications network 414 (FIG. 4)) associated with electrical activity of brain states and corresponding moods to determine the current mood of the user.

For example, the particular frequency range of the brain activity of a user may correspond to a particular mood (e.g., sadness). This correspondence may be recorded in a database which records the various frequency ranges of different moods of the user and/or all users. To determine the correspondence, the media guidance application may input the determined frequency range of the brain activity of the user into the database. The database may then identify all available moods that correspond to the determined frequency range. For example, a brain state has a frequency of 4 to 8 Hz, the database may identify moods (e.g., happiness) corresponding to a frequency of 4 to 8 Hz. The database may then output the results, which indicate an identified mood that corresponds to the current frequency range of the brain activity of the user.

In some embodiments, the control circuitry 304 may use the location information of the brain activity detectors to determine the brain state. For example, in reference to configuration 1030 of user device 900 illustrated in FIG. 10, the control circuitry 304 may determine that the brain activity detectors are detecting brain signals from the occipital lobe (e.g., at position O1), and from the frontal lobe (e.g., at position Fp1). Based on this information about the brain portions, control circuitry 304 may adjust the search and matching of brain state to those associated with eye blink activity states (corresponding to the occipital lobe), and to those associated with moods (corresponding to the frontal lobe). Control circuitry 304 next proceeds to step 1355.

At step 1355, media guidance application cross-references the position of electrodes and the brain state to a database of media guidance application operations. Control circuitry 304 may cross-reference data associated with the brain state of a user (e.g., a frequency range, an electrical activity of the muscles near the brain, an electrical activity of the brain, and/or a threshold range) with a database associated with data related to brain states and corresponding moods. The media guidance application may divide the cross-reference into two steps. The media guidance application may first perform a cross-reference, using a cranium location/brain portions database, based on the position of the user device or brain activity detectors (e.g., position Fp1, F3, T3, O1, etc.) to determine corresponding brain regions (e.g., frontal lobe, temporal lobe, etc.) of the sub-components of the user device (e.g., brain activity detectors in in sub-components in any of sub-components 925, 930, 935, 940, 945, 950, 955, and 960). The media guidance application may then perform a cross-reference, using a brain portion/operations database, based on the determined brain portions from the first step to determine a set of media guidance application operations. Control circuitry next proceeds to step 1360.

At step 1360, media guidance application determines whether the set of media guidance application operations corresponds to the determined first and second positions of the first and second brain activity sensors, and determined brain state. In some embodiments, the control circuitry 304 performs the cross-reference described in step 1355 above, and determines a quantitative metric of the cross-reference in order to determine whether the media guidance application operations correspond. For example, control circuitry 304 may compare the determined quantitative metric to a threshold. If control circuitry 304 determines that the metric corresponds to the threshold, the set of media guidance application operations corresponds to the determined brain state and the determined first and second positions of the first and second brain activity sensors, respectively. Control circuitry proceeds to step 1365. If the control circuitry determines that the set of media guidance application operations does not correspond to the determined position and brain state, the control circuitry proceeds to step 1370.

At step 1365, the media guidance application enables a set of determined features. The particular media guidance application operation performed may be based on the brain state. For example, the set of media guidance application operations may be channel changing operations, based on brain signals measured from the occipital lobe. The control circuitry may determine that the user has a first eye blink pattern associated with a first eye blink brain state, and in response, change the channel upwards. The control circuitry may determine that the user has a second eye blink pattern associated with a second eye blink brain state, and in response, change the channel downwards. For example, the set of media guidance application operations may be recommendation of programs, based on brain signals measured from the frontal lobe. The control circuitry may determine that the user is in a happy mood, and provide recommendations of programs associated with a happy mood (e.g., programs of the comedy genre). Control circuitry 304 then proceeds to step 1305 to repeat the process.

At step 1370, the media guidance application has determined that the set of media guidance application operations does not correspond to the brain state and positions of brain machine interfaces. For example, the result of the cross-reference in step 1355 may be too low. Control circuitry 304 may generate an output signal for display to the user indicating that no media guide operations were found. In response, the process may repeat to step 1305.

The above-described embodiments of the disclosure are presented for purposes of illustration and not of limitation, and the disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real-time. It should also be noted, the systems and/or methods described above may be applied to, or used in accordance with, other systems and/or methods.

What is claimed is:

1. A method for providing media guidance application operations to a user, the method comprising:
    determining whether a first biometric measurement is detectable;
    in response to determining that the first biometric measurement is detectable, determining a first position of a user device on the user's body where the first biometric measurement is detected;
    comparing the determined first position of the user device with a first database of sets of media guidance application operations that are accessible based on positions of user devices to determine a first set of interactive media guidance application operations that are accessible by the user based on the determined first position of the user device;
    providing to the user the first set of interactive media guidance application operations that are accessible by the user based on the determined first position of the user device; and
    generating for display a message instructing the user to re-position the user device to a second position in order to access a second set of interactive media guidance application operations that are accessible from the second position.

2. The method of claim 1, further comprising:
    determining whether a second biometric measurement is detectable; and
    updating the determined first position of the user device to correspond with the detection of the first biometric measurement and the second biometric measurement.

3. The method of claim 1, wherein determining the first position of the user device further comprises:
    cross-referencing the detection of the first biometric measurement with a second database listing positions of the user device that correspond to different biometric measurements being detectable to determine the first position of the user device.

4. The method of claim 1, wherein the first biometric measurement comprises a measurement of at least one of an alpha band constituent signal, a beta band constituent signal, a delta band constituent signal, a gamma band constituent signal, and a theta band constituent signal.

5. The method of claim 1, wherein the user device is a circular fixture, and the method further comprises determining whether the first biometric measurement is detectable by using a brain activity detector disposed on the circular fixture.

6. The method of claim 1, wherein the user device is shaped as jewelry.

7. The method of claim 1, wherein the first position of the user device corresponds to a reference location on a cranium of the user.

8. The method of claim 1, wherein the first position corresponds to at least one of a frontal lobe, parietal lobe, occipital lobe, and temporal lobe of the user's brain.

9. The method of claim 1, further comprising determining a brain state of the user based on the first biometric measurement.

10. A system comprising:
    storage circuitry configured to store a first database of sets of media guidance application operations that are accessible to a user device based on a positioning of the user device on a user; and control circuitry configured to:
  determine whether a first biometric measurement is detectable;
  in response to determining that the first biometric measurement is detectable, determine a first position of the user device on the user's body where the first biometric measurement is detected;
  compare the determined first position of the user device with the first database to determine a first set of interactive media guidance application operations that are accessible by the user based on the determined first position of the user device;
  provide to the user the first set of interactive media guidance application operations that are accessible by the user based on the determined first position of the user device; and
  generate for display a message instructing the user to re-position the user device to a second position in order to access a second set of interactive media guidance application operations that are accessible from the second position.

11. The system of claim 10, wherein the control circuitry is further configured to:
  determine whether a second biometric measurement is detectable; and
  update the determined first position of the user device to correspond with the detection of the first biometric measurement and the second biometric measurement.

12. The system of claim 10, wherein the control circuitry is further configured to:
  cross-reference the detection of the first biometric measurement with a second database listing positions of the user device that correspond to different biometric measurements being detectable to determine the first position of the user device.

13. The system of claim 10, wherein the first biometric measurement comprises a measurement of at least one of an alpha band constituent signal, a beta band constituent signal, a delta band constituent signal, a gamma band constituent signal, and a theta band constituent signal.

14. The system of claim 10, wherein the user device is a circular fixture, and the system further comprises:
  a first brain activity detector disposed on the circular fixture; and
  wherein the control circuitry is further configured to determine whether the first biometric measurement is detectable by using the first brain activity detector disposed on the circular fixture.

15. The system of claim 10, wherein the user device is shaped as jewelry.

16. The system of claim 10, wherein the first position of the user device corresponds to a reference location on a cranium of the user.

17. The system of claim 10, wherein the first position corresponds to at least one of a frontal lobe, parietal lobe, occipital lobe, and temporal lobe of the user's brain.

18. The system of claim 10, wherein the control circuitry is further configured to determine a brain state of the user based on the first biometric measurement.

* * * * *